(12) United States Patent
Seifarth et al.

(10) Patent No.: US 7,115,367 B1
(45) Date of Patent: Oct. 3, 2006

(54) METHOD FOR THE SPECIFIC DETECTION AND IDENTIFICATION OF RETROVIRAL NUCLEIC ACIDS/RETROVIRUSES IN A SPECIMEN

(75) Inventors: Wolfgang Seifarth, Nussloch (DE); Christine Leib-Mösch, München (DE); Corinna Baust, Walldorf (DE)

(73) Assignee: Ruprecht-Karls-Universität Heidelberg, Heidelberg (DE)

( * ) Notice: Subject to any disclaimer, the term of this patent is extended or adjusted under 35 U.S.C. 154(b) by 0 days.

(21) Appl. No.: 10/009,705

(22) PCT Filed: Apr. 4, 2000

(86) PCT No.: PCT/DE00/01071

§ 371 (c)(1),
(2), (4) Date: Nov. 28, 2001

(87) PCT Pub. No.: WO00/68435

PCT Pub. Date: Nov. 16, 2000

(30) Foreign Application Priority Data

May 8, 1999 (DE) ............................... 199 21 419

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search .............. 435/6, 435/91.2; 536/23.1, 24.3
See application file for complete search history.

(56) References Cited

U.S. PATENT DOCUMENTS 5,478,724 A    12/1995    Morse et al.

FOREIGN PATENT DOCUMENTS

| DE | 196 05 279.3 | | 8/1997 |
|---|---|---|---|
| EP | 0 229 701 A | | 7/1987 |
| EP | 0 789 081 A | | 8/1997 |
| WO | WO 93/25707 A | | 12/1993 |
| WO | WO 95 02704 A | | 1/1995 |
| WO | WO 95/21256 | | 8/1995 |
| WO | WO97/27332 | * | 7/1997 |
| WO | WO 98/23755 | | 6/1998 |
| WO | WO 99/05527 | | 2/1999 |

OTHER PUBLICATIONS

Mack et al: "A sensitive Method for the Identification . . . " Proc. Natl. Acad. Sci. USA, vol. 85, No. 18, 1988, pp. 6977-6981.
Seifarth et al.: "Retrovirus-like particles released from the human breast . . . " Journal of Virology, vol. 69, No. 10, 1995, pp. 6408-6416.
Donehower et al.: "The use of priemers from highly conserved pol regions . . . " Journal of Virological Methods, vol. 28, No. 1, 1990, pp. 33-46.
Rose et al.: "Consensus-degenrate hybrid oligonucleotide . . . " Nucleid Acids Research, vol. 26, No. 7, Apr. 1, 1998, pp. 1628-1635.
Wichman et al: "In search of retrotransposons exploring the . . . " BioTechniques, vol. 13, No. 2, 1992, pp. 258-263, 265.
Medstrand et al: "Characterization of Novel Reverse Transitase Encoding Human Endogenous . . . ", in: Journal of Virology, Nov. 1993, pp. 6778-6787.
Takeuchi et al.: "Retroviral Pseudotypes Produced by Rescue of a Moloney Murine Leukemia Virus . . . ", in Virology 186, pp. 792-794 (1992).
Vogetseder et al.: "Antibodies in Human Sera Recognizing a Recombitant Outer . . . ", in: Aids Research and Human Retroviruses, vol. 9, No. 7, 1993.
Sherwin et al: "Rescue of Endogenous 30S Retroviral Sequences . . . ", in: Journal of Virology, May 1978, pp. 257-264.
Shih et al.: "Detection of Multiple, Novel Reverse Transcriptase Coding Sequences in Human . . . ", in: Journal of Viroloogy, Jan. 1989, pp. 64-75.
Anderson et al.: "Differential Expression of Human Endogenous Retroviral Sequences . . . ", in: Ais Research and Human Retrovirus, vol. 12, No. 9, 1996.

(Continued)

*Primary Examiner*—Ethan Whisenant
(74) *Attorney, Agent, or Firm*—Henry M. Feiereisen; Ursula B. Day

(57) ABSTRACT

The invention relates to a method for specifically detecting and identifying retroviral nucleic acids/retroviruses in any item to be examined using RT-PCR and reverse dot blot hybridization (RDBH) as well as to diagnosis kits for carrying out said method. The invention also relates to retrovirus-specific, oligonucleotide/primer mixtures (MOP) which comprise forward primers and reverse primers and which are provided for generating amplification products of retrovirus-specific nucleic acids from the item to be examined. These inventive primary mixtures (MOP-ABD, MOP-C) are comprised of retrovirus-specific, degenerated oligonucleotides which correspond to the highly conserved regions located within the reverse transcriptase gene (RT-gene) of all known human retroviruses and which have a head or extension sequence consisting of a clamping and interface sequence. The invention also relates to retrovirus-specific probes for the RDBH, whereby defined quantities of synthetically produced, precisely defined nucleic acid sequences are concerned which stem from the reverse transcriptase gene of those retroviruses already characterized, against which the item to be examined should be tested, and which do not overlap at all with the nucleotide sequences of the forward primers and reverse primers used in the PCR or RT-PCR.

14 Claims, 4 Drawing Sheets

OTHER PUBLICATIONS

Poch et al.: "Identification of four conserved motifs among the RNA-dependnet polymerase . . . ", in: The EMBO Journal, vol. 8, No. 12, pp. 3867-3874, 1989.

Fodor et al.: "Light-Directed, Spatially Addressable Parallel Chemical Synthesis", in: Research Article, Feb. 15, 1991, pp. 767-773.

McClure et al.: "Sequwence Similarity between Borna Disease Virus p40 and a Duplicated . . . ", in: journal of Virology, Jun. 1992, pp. 6572-6577.

Seifarth et al.: "Proviral Structure, Chromosomal Location, and . . . ", in: Journal of Virology,, Oct. 1998, p. 8384-8391.

Scolnick et al.: "Defective Retrovirus-Like 30S RNA Species of Rat and Mouse Cells . . . ", in: Journal of Virology, Mar. 1979, p. 964-972.

Herrmann et al.: "PCR and reverse dot hybridization for the detection od endogenous . . . ", in: Journal of Virological Methods 46 1994), p. 333-348.

Patience et al.: "Infection of human cells by an endogenous retrovirus of pigs", in: Nature Medicine, vol. 3, No. 3, Mar. 1997.

Xiong et al.; "Origin and evolution of retroelements based upon their reverse transcriptase . . . ", in: The EMBO Journal, vol. 9, No. 10, pp. 3353-3362, 1990.

Tuke et ak.: "Development of a pan-retrovirus detection system for multiple sclerosis studies", in: Acta Neurol Scand 1997, Suppl. 169, p. 16-21.

Kalden et al.: "Autoimmune Diseases in Humans, e.g. Autoimmune Rheumatic Diseases", in: Intervirology 1993, vol. 35, pp. 176-185.

Takeuchi et al.: "Host Range and Interference Studies of Three Classes of Pig . . .", in: Journal of Virology, Dec. 1998, pp. 9986-9991.

Sauter et al.: "Human Endogenous Retrovirus K10: Expression of Gag Protein and . . . " in: Journal of Virology, Jan. 1995, p. 414-421.

Conrad et al.: "A Human Endogenous Retroviral Superantigen as Candidate Autoimmune . . . " in: Cell, vol. 90, p. 303-313, Jul. 25, 1997.

Elisabeth Herniou et al.: "Retroviral Diversity and Distribution in Vertebrates", Journal of Virology, vol. 72, no. 7, Jul. 1998, pp. 5955-5966.

Antoinette v.d. Kuyl et al.: "Full-Length Proviruses of Baboon Endogenous Virus . . . ", Journal of Virology, vol. 69, No. 9, Sep. 1995, pp. 5917-5924.

Chemical Abstracts, vol. 131, 1999, pp. 258.

Chemical Abstracts, vol. 124, 1996, p. 358.

* cited by examiner

METHOD FOR THE SPECIFIC DETECTION AND IDENTIFICATION OF RETROVIRAL NUCLEIC ACIDS/RETROVIRUSES IN A SPECIMEN

BACKGROUND OF THE INVENTION

The invention relates to a method for the specific detection and identification of retroviral nucleic acids/retroviruses in an arbitrary specimen and a diagnosis kit for implementing this method. It also relates to retrovirus-specific probes for reverse dot blot hybridisation and retrovirus-specific oligonucleotide primer mixtures (MOP) comprising forward and reverse primers for producing amplificates of retrovirus-specific nucleic acids from the specimen.

Exogenous and endogenous retroviruses (HERV) are etiological agents for a multiplicity of tumorigenic diseases in humans and animals. They are involved in the formation of tumours and leukaemias in numerous animal models but also in humans (HTLV-I and II). Others also cause immunodeficiency diseases (HIV). Present research indicates that retroviruses may also play a role as triggers of autoimmune diseases (Kalden and Herrmann, 1993) and neuronal degenerative diseases such as multiple sclerosis (Tuke et al. 1997). Intensive research in the field of endogenous and exogenous retroviruses has so far led to the continual discovery of new retroviral sequences in the human genotype whose expression could possibly be associated with specific diseases. For example, the expression of Gag proteins of the HERV-K family is associated with almost all forms of testicular and ovarian germinomas (Sauter et al. 1995). Antibodies against HERV-K Env protein were detected in human sera (Vogetseder et al. 1993). The HERV-K-IDDM env gene which was isolated from patients with type-1 diabetes possibly codes for an endogenous superantigen (Conrad et al. 1997).

Statistically reliable studies using large groups of patients are required to correlate specific diseases with the activity of specific endogenous or exogenous retroviruses. The expenditure in time and money required for this using the known methods of detection according to the prior art is immense.

The increasing use of retroviral vector systems in human gene therapy casts doubts on the safety from undesirable side effects (genome changes in the target cells, transmission of undesirable viruses). Thus, a certain percentage of undesirable gene sections of endogenous or foreign retroviruses are also co-packaged in the retroviral particles for therapeutic application in packaging cell lines (Co-packaging, Sherwin et al. 1987, Scolnick et al. 1979, Takeuchi et al. 1992). For example, transcripts of certain endogenous retroviruses, such as those present in related form in the genome of packaging cell lines, have been detected in retrovirus-like particles (pseudotypes) of the breast cancer cell line T47D (Seifarth et al. 1995, 1998). The packaging of such undesirable retroviral sequences can lead to the recombination and formation of new retroviruses having modified, possible pathogenic properties. The re-integration of such recombinant retroviruses in the genome of the target cells can lead to insertion mutagenesis and consequently to inactivation of important genes of the cell cycle and possibly to tumorgenesis.

For this reason it is necessary to conduct quality control of the gene vector preparations to be used for gene therapy using a sensitive test system. This could prevent any undesirable retroviral sequences from being transfused. In the event of positive detection, a vector preparation could be subjected to suitable purification (purging) before being administered to the patient. The methods known according to the prior art are not suitable for such an application.

A controversial issue at the present time is the use of animal organs for transplantation in humans (xenotransplantation). For example, as a result of the shortage of suitable donors, heart valves from pigs are being increasingly transplanted in humans. The transplantation of heart, liver and kidney transplants is also planned. However, recent research has shown that within the transplantation framework and the associated immunosuppression by medication, endogenous or exogenous retroviruses so far suppressed in the donor organ can become activated in the recipient. As has already been demonstrated experimentally, these retroviruses of animal origin are pathogenic for certain human cell types (xenotropism) and could thus lead to a serious systemic disease of the organ recipient. In cases where pathogenic infectious virus particles are formed, transmission to uninvolved third parties (epidemic) cannot be excluded. Last but not least, recombinations of retroviruses of animal origin with endogenous human retroviruses could result in new pathogenic virus recombinants with completely new host tropisms.

There is thus a need for fast, reliable and at the same time favourably priced detection systems which could be used to test the transplant carrier for infection with retroviruses of animal origin on a regular basis.

A number of methods for direct and indirect virus detection are available for the detection of viral infections in the prior art. For the direct detection of virus particles, products of viral replication (viral antigens) or an immune response directed against the virus (antiviral antibodies) these include electron microscopy (EM), staining of viral proteins with fluorescent antibodies, "enzyme-linked immunosorbent assay" (ELISA) and radioimmunoassay (RIA). Molecular biological methods such as nucleic acid hybridisations with virus-specific gene probes (dot-blot, southern-blot, northern-blot) and polymerase chain reaction (PCR) with virus-specific primers are being conducted increasingly to directly detect the virus and its nucleic acids.

In the indirect methods it is usually not the viruses themselves but their after-effects that are detected, i.e. the changes (cytopathic effects) in cells induced by a virus replication. This must usually be conducted in an in vitro cell culture system tailored to the virus to be detected. This requires living cells in which the virus to be detected can replicate. Depending on the type of virus, cell cultures, organ cultures, embryonated chick eggs or even laboratory animals are required for the detection. The manifestation of the cytopathic effect (cell lysis, focal or diffuse cell growth, syncytium formation, rounding) and the host spectrum of the virus are used as indices to identify the virus. Frequently however, a precise identification can only be made in combination with serological or molecular biological methods (PCR).

The relatively low sensitivity of some direct methods of detection (EM, antibody staining) means that the specimen must contain a certain quantity of virus for a successful detection or it must be enriched by suitable methods (ultra-centrifuging). If this is not practicable, the virus must be preliminarily cultured in a special in vitro cell culture system. Since many viruses possess special host cell tropisms, a special test system is required for each virus to be tested. This results in high laboratory costs, their evaluation is very time-consuming in some cases and requires very great experience.

Serological methods (ELISA, RIA) are generally highly sensitive and have developed into the current gold standard in virus diagnosis. However, the disadvantage of all serological methods is that a specific antibody is required for each virus to be tested. In one test run the sample to be studied can thus only be tested for one putative virus. Studies of entire expression patterns using these methods can only be made at great expense in time and cost.

Developments in the field of molecular biology have led to the development of new methods of detection (hybridisations, PCR) which possess similar sensitivity to serological antigen methods of detection. In this case also, the detection success stands or falls by the availability of virus-specific gene probes (hybridisation) or oligonucleotides (PCR). Since the use of several probes or PCR primers is limited because of non-specific interactions in a reaction formulation, many experiments must be conducted in parallel to detect complex expression patterns.

In view of the circumstances described previously, the problem for the present invention was to provide an efficient and reliable, and at the same time fast method for the multiple detection of endogenous and exogenous retroviruses of human and animal origin.

SUMMARY OF THE INVENTION

This problem is solved using a method of the type specified initially which is characterised in that it comprises the following measures:

Isolation of nucleic acids, namely DNA and/or RNA from the specimen,
  carrying out a PCR using the isolated DNA or an RT-PCR using the isolated RNA using one or both the primer mixtures MOP-ABD and MOP-C described hereinafter, each consisting of forward primers and reverse primers, whose forward and reverse primers are degenerated oligonucleotides having the nucleotide sequences reproduced in the sequence protocols SEQ ID NO.1 to NO.4 according to the IUPAC nomenclature and a so-called "head" at the 5'-end of these nucleotide sequences, whereby the forward primers of the MOP-ABD mixture exhibit the nucleotide sequences in accordance with SEQ ID NO.1, namely the nucleotide sequences: "head"-ARAGTNYTDY-CHCMRGGH, with 3456 degenerations, the reverse primers of the MOP-ABD mixture exhibit the nucleotide sequences in accordance with SEQ ID NO.2, namely the nucleotide sequences: "head"-NWD-DMKDTYATCMAYRWA, with 27648 degenerations, the forward primers of the MOP-C mixture exhibit the nucleotide sequences in accordance with SEQ ID NO.3, namely the nucleotide sequences: "head"-TKKA-MMSKVYTRCYHCARGGG, with 3072 degenerations, and the reverse primers of the MOP-C mixture exhibit the nucleotide sequences in accordance with SEQ ID NO.4, namely the nucleotide sequences: "head"-MDVHDRBMD-KYMAYVYAHKKA, with 8192 degenerations, whereby "head" stands for a nucleotide sequence which comprises an interface for a restriction enzyme and a so-called clamp sequence (for stabilisation of the interface sequence) at the 5' end of this interface,
  purging the (RT)-PCR amplificates obtained and using these in an RDBH method using immobilised RDBH probes which each (per probe) comprise synthetic oligonucleotides whose nucleotide sequence corresponds to the retroviral nucleotide sequence of the retrovirus-specific reverse transcriptase gene of the virus type to be detected with the relevant dot or a section of such a retroviral nucleotide sequence and shows no overlapping with the nucleotide sequences of the forward primers and reverse primers used in the PCR or RT-PCR.

The object of the present invention is thus a method for detecting retroviral nucleic acids in a sample whereby first all nucleic acids (RNA and DNA) are extracted from the specimen using common methods known to the specialist. Here a distinction is made between DNA and RNA. The isolation of genomic DNA is sufficient to detect retroviruses (proviruses) already integrated in the host cell genome. If the activatability of so far inactive retroviruses, the transcription activity of endogenous retroviruses or the identity of retroviral particles are to be studied, polyadenylate messenger RNA (mRNA) free from genomic DNA must be isolated. If mRNA is used as the starting material, this mRNA must be transcribed into complementary DNA (cDNA) in vitro by means of reverse transcriptase and can then be used as matrices for the following PCR. This combination of reverse transcription and PCR is generally described as RT-PCR.

The isolated nucleic acids are then subjected to a one-step PCR using primer mixtures according to the invention (MOP-ABD, MOP-C) consisting of retrovirus-specific, degenerated oligonucleotides corresponding to the highly conserved regions within the reverse transcriptase gene (RT gene) of all known human retroviruses (MOP, Shih et al. 1989, Donehower et al. 1990). In this PCR all retrovirus-specific 'reverse transcriptase' homologous sequence sections contained in the specimen are amplified. As a result an amplificate mixture of short retroviral DNA fragments is obtained whose composition reflects the frequency of all retroviral nucleotide sequences to be detected in the specimen. The amplificates are either labelled during the PCR reaction or after this reaction, preferably radioactively, but equally well non-radioactively according to choice (e.g. with biotin or digoxigenin). These labelled amplificates are then used as probes in a hybridisation method (RDBH method) using filter membranes or bio-chips with applied retrovirus-specific oligonucleotides as probes.

The head or extension sequence of the primer oligonucleotides according to the invention consisting of clamp and interface sequence first has the positive effect that it favourably influences the primer matrix binding kinetics so that the PCR products formed in the first PCR cycle are amplified substantially more efficiently in the following cycles. This has the advantage that retroviral matrices are then amplified themselves or can be amplified if the exactly matching primer is not present in the primer mixture. The interface also has the advantage that it facilitates cloning if necessary.

It basically holds that the length of the head or extension sequence should not exceed half the length of the complete primer nucleotide sequence.

An important component of the method according to the invention are the RDBH probes used for the reverse dot blot hybridisation (RDBH) which comprise specific quantities of synthetically produced, exactly defined nucleic acid sequences from the reverse transcriptase gene of those retroviruses already characterised against which the specimen is to be tested. These retrovirus-specific RDBH probes are applied to defined fields (dots) of the RDBH support whereby this can be conventionally used filter membranes having dimensions of several centimeters and also so-called bio-chips having dimensions of a few millimeters (microarray technology). In the case of filter membranes the probes are preferably linked to these supports covalently by UV crosslinking (e.g. using the commercially available UV radiation source 'Stratalinker™', Stratagene).

In the case of DNA chips, oligonucleotide probes are synthesised in situ and fixed in precisely defined positions on a solid support using photolithographic methods (similar to engraving) (e.g. by using perforated masks specific areas of the chip are illuminated to activate photosensitive chemical groups). The support, preferably a glass or nylon surface of approximately 1 cm² forms the hybridisation unit. Each hybridisation unit can contain a very large number of different oligonucleotide probes (up to 400,000). As a result many thousand different sequences can be analysed simultaneously. For each probe all sequence alternatives are presented on the chip and a single one must be recognised by the specimen to be tested. The hybridisation of probe and target sequence (in the specimen) is detected by measuring the amplificate marker intensity. The intensity is proportional to the extent of the hybridisation between probe and target sequence. Each target sequence is identified according to its hybridisation position on the chip. The DNA chip technique was developed by FODOR et al. (Science 251, 767–773, 1991) and is known in the prior art (see V. Oeding et al. 1999, *HYGIENE UND MIKROBIOLOGIE* 1/99, pp. 55–57 and G. Ramsay 1998, *NATURE BIOTECHNOLOGIE*, Vol. 16, 1998, pp. 40–44).

Hybridisation should take place under highly stringent conditions matched to the length of the probes and the hybridised supports (filter membranes or chips) should then be washed under highly stringent conditions. In cases where the PCR amplificates are radioactively labelled, the identity of the detectable retroviruses can then be identified after exposing the filter membranes on an x-ray film using the signal pattern of the autoradiograms.

The method according to the invention can be used for the multiple detection and identification of all human and/or animal-specific retroviral nucleic acids/retroviruses known so far in cell cultures, cell culture residues or body samples or other specimens of biological origin. The only prerequisite is that certain genome sections of the retroviruses to be detected, namely the conserved sequence regions of the reverse transcriptase are known with respect to their DNA nucleotide sequence. This prerequisite is satisfied since the corresponding nucleotide sequences of exogenous and endogenous human retroviruses are generally accessible as gene bank data.

The method according to the invention for the first time opens up the possibility of providing a universal retrovirus detection system with which the entire spectrum (=expression pattern) of all active endogenous and exogenous retroviral nucleotide sequences in the specimen (body sample) can be determined in a single experiment. In particular, this detection system can also be used to carry out statistically reliable studies using arbitrarily large groups of patients and if appropriate correlations existing between specific diseases and the activity of specific endogenous or exogenous retroviruses can be established therefrom. In the event of a proven correlation between a specific retroviral expression pattern and a specific disease, this test system can also be used for the early identification or to assess the personal genetic risk for such a disease.

Another very decisive advantage of the method is that the sequences of the PCR primers (MOP) according to the invention, i.e., the degenerated oligonucleotides of the primer mixtures used to amplify the retrovirus-specific RT gene sections to be identified in the specimen do not overlap with the sequences of the synthetic virus-specific oligomers used as dot blot probes. The PCR primer sequences contribute approximately half the final amplificate length. If these sequence sections were also contained in the dot blot probes (cf. Herrmann and Kalden, 1994), this would lead to considerable restrictions in the prediction capability of the test since the amplificates would then hybridise to a certain extent with all dot blot probes on the filter membrane. It is an advantage of the method according to the invention that this undesirable effect is impeded by using synthetic, precisely defined, homogenous oligonucleotide preparations for both the forward and reverse primers and for the RDBH probes.

The nucleotide sequences of all exogenous and endogenous retroviruses characterised so far (HERV) are published in gene banks. From these suitable nucleotide sequences can be derived for the synthesis of virus-specific oligomers as dot blot probes. In principle, corresponding oligomers of all these sequences can be dotted onto a single filter membrane. Consequently, it is possible to test a specimen for the entire spectrum of retroviruses known so far in a single experiment. Compared with the prior art whereby its own diagnostic test, especially a serological test using a special antibody, must be carried out to identify each putative virus in a sample, the method according to the invention thus represents significant progress.

As a result of the known higher sensitivity of PCR and the possibility of repeated amplification of PCR products, the method according to the invention also attains a detection limit which is barely achieved by any other test system.

In a preferred embodiment of the method according to the invention the "head" or extension section of the primer nucleotides according to the invention consists of the nucleotide sequence GAAGGATCC whereby the nucleotide series GM is a so-called 'clamp' and the nucleotide series GGATCC represents the interface for the restriction enzyme BamHI. The head or extension sequence has proved very good in practice. In principle, however, the head sequence can also consist of any arbitrary nucleotide sequence provided that the primer annealing kinetics is not negatively influenced.

The nucleotide sequences of the synthetic oligonucleotide of the RDBH probes are preferably selected so that they correspond to the retroviral nucleic acid region of the reverse transcriptase gene between the highly conserved motifs V L P Q G and Y M/V D D I/V/L L or to a section of this region i.e., they match and/or (experimentally) can hybridise with it.

Since the efficiency of an oligonucleotide synthesis decreases with the length of the oligonucleotide to be synthesised, a variant of the method according to the invention is provided in which a mixture of equimolar quantities of two comparatively short-chained synthetic oligonucleotides is used as immobilised RDBH probes in each case (i.e. for each probe or each dot). These correspond together or one after the other to a longer, preferably approximately 90 base pairs (bp) long, section of the nucleic acid region of the reverse transcriptase gene between the highly conserved motifs V L P Q G and Y M/V D D I/V/L L.

In an embodiment that has proved very useful in practice, these two short-chain oligonucleotides are approximately the same size or the same length and preferably comprise approximately 45 base pairs.

The invention is explained subsequently in greater detail with reference to examples of embodiment and relevant drawings and tables.

The abbreviations used are as follows:
BaEV=baboon endogenous retrovirus;
ERV=endogenous retrovirus;
ERV9=endogenous retrovirus type 9.
GaLV=gibbon ape leukaemia virus;

HERV=human endogenous retrovirus;
HIV=human immunodeficiency virus;
HML=human mouse mammary tumour virus-like sequence;
HPLC=High Performance Liquid Chromatography
HRV5=human (exogenous) retrovirus type 5;
HTLV-1=human adult T-cell leukaemia virus type 1;
LINE=long, disperse (scattered) DNA sequence element;
MMTV=mouse mammary tumour virus;
MoMuLV=Moloney mouse leukaemia virus;
MOP=Primer mixture of degenerated oligonucleotides comprising forward and reverse primers
MPMV=Mason Pfizer monkey virus;
PCR=polymerase chain reaction;
PERV=porcine endogenous retrovirus;
PBMNC=peripheral blood mononuclear cells;
RDBH=reverse dot blot hybridisation;
RT=reverse transcriptase.

Table 1: Retrovirus-type ABD and type C specific primer mixtures MOP-ABD and MOP-C according to the invention which each contain forward and reverse primers and comprise degenerated oligonucleotides. The standardised single-letter abbreviation code of the IUPAC nomenclature has been used to describe the degenerated oligonucleotide sequences (see European Journal of Biochemistry 150: 15, 1985). Both the forward primer and the reverse primers are shown in the 5'-3' direction following the IUPAC conventions and relative to the DNA strand. The degree of degeneration, in other words the number of different specific embodiments of this primer that can be obtained by synthesis, is given in each case in the form of the theoretically calculated number of different oligonucleotides.

Table 2: Immobilised synthetic retrovirus-specific oligonucleotide probes for producing dot blot membranes. A mixture of equimolar quantities of both partners of an oligonucleotide pair which corresponds to a 90 bp long section of a retrovirus-specific reverse transcriptase was prepared for each spot or dot. In each case 100 picomole of these mixtures was applied to the membrane in the configuration corresponding to the code shown. A dilution series of human genomic DNA (8E–8H) and oligonucleotide primer mixtures (8I–8L) was applied to the filter for internal standardisation of the hybridisation and autoradiography. For each oligonucleotide sequence used on the filter the gene bank access number and the first author are given where available.

Table 3: Classification of retrovirus-specific oligonucleotide dot blot probes: From 61 representative members of all known human exogenous and endogenous retroviruses the nucleotide sequence of the appropriate reverse transcriptase gene in the region between the highly conserved domains V L P Q G and Y M/V D D I/V/L L was used to synthesise dot blot probes (Shih et al. 1989, Donehower et al. 1990). In the experiment shown here 21 retroviral nucleotide sequences from type ABD (HERV-K superfamily), 19 retroviral nucleotide sequences from type C, 1 retroviral nucleotide sequence from type D and 7 nucleotide sequences related to the human foamy virus were used. Also tested were a human LINE-1 sequence (3L) and 6 exogenous human retroviruses (6E–6J), as well as five probes which correspond to a mammal C type retrovirus and a probe which corresponds to a mammal B type retrovirus (7E–7J).

Asterisks indicate nucleotide sequences related to HERV transcripts which were found in patients with multiple sclerosis and patients with systemic lupus erythematosus.

The reverse dot blot hybridisation (RBDH) was carried out under standard conditions using DNA fragments which had been amplified using the primer mixtures of degenerated oligonucleotides according to the invention, namely MOP-ABD (Table A) or MOP-C (Table B) or the combination MOP-ABD/MOP-C (Table C).

Figure 4:
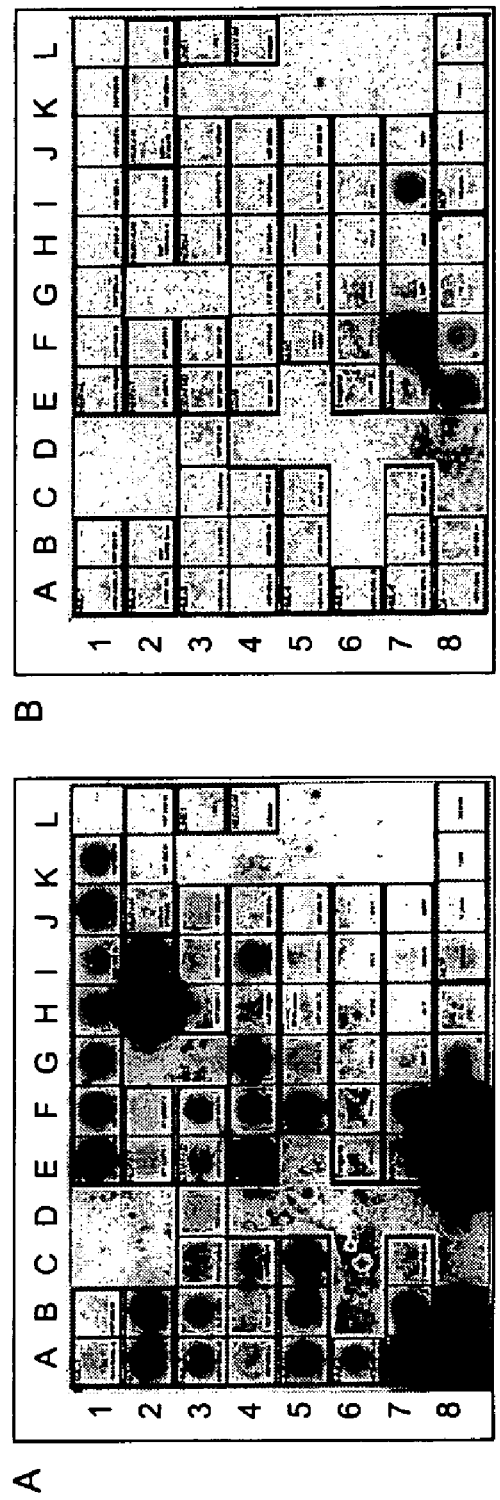

FIG. 4. HERV expression in human PBMNCs after adding a cloned DNA fragment that contains a PERV RT gene. Less than 10 copies of a porcine endogenous retrovirus (PERV) type A DNA (Patience et al. 1997) could be detected and identified under standardised test conditions (Table A, filter code 7F). Under the stringent conditions used no cross hybridisation of HERVs with porcine-specific amplification products obtained from a porcine DNA matrix were observed (Table B).

DETAILED DESCRIPTION OF PREFERRED EMBODIMENTS

EXAMPLE 1

RNA Preparation

Total RNA was extracted from peripheral blood mononuclear cells of a healthy blood donor using the guanidine isothiocyanate/caesium chloride (GIT/CsCl) ultracentrifugation protocol proposed by Sambrook et al. (1989) and dissolved in distilled water treated with diethylpyrocarbonate (DEPC). The mRNA was then enriched using conventional methods e.g. using the commercially available enrichment kit 'Dynabeads™ paramagnetic particles' according to the manufacturer's instructions (Dynal, Hamburg, Germany). The nucleic acid concentration was determined by means of spectrometry at 260 nm. In order to check for any contamination with genomic DNA, 50 ng of each mRNA preparation was used directly, i.e., without first having undergone a reverse transcription, in a polymerase chain reaction (PCR) using the primer mixtures of degenerated oligonucleotides (MOP) according to the invention. Only those preparations which showed no DNA traces were used for the actual PCR. Those preparation formulations for which some DNA contamination could be detected were treated with 100 units/μg RNase-free DNase (Roche Diagnostics, Mannheim Germany) in 100 mM pH 5.0 sodium acetate, 5 mM $MgSO_4$, until the control PCR yielded a negative result.

EXAMPLE 2

Preparation of MOP-ABD and MOP-C Primer Mixtures According to the Invention for PCR Table 1 shows preferred MOP-ABD and MOP-C primer mixtures using the IUPAC nomenclature familiar and commonly used in specialist circles. Each of the primer mixtures contains a plurality of different forward and reverse primers. The forward primers of the MOP-ABD primer mixture exhibit the general nucleotide sequence GAAGGATCCAR-AGTNYTDYCHCMRGGH which comprises 3456 degenerations, i.e. 3456 different specific nucleotide sequences. The reverse primers of the MOP-ABD primer mixture exhibit the nucleotide sequence GAAGGATCCNWD-DMKDTYATCMAYRWA which comprises 27648 degenerations, i.e. 27648 different specific nucleotide sequences. The forward primers of the MOP-C primer mixture are characterised by the general nucleotide sequence GAAG-GATCCTKKAMMSKVYTRCYHCARGGG, which comprises 3072 degenerations, i.e. 3072 different specific nucleotide sequences and the reverse primers of the MOP-C primer mixture exhibit the nucleotide sequence GAAG-GATCCMDVHDRBMDKYMAYVYAHKKA which comprises 8192 degenerations, i.e. 8192 different specific nucleotide sequences.

Figure 1:
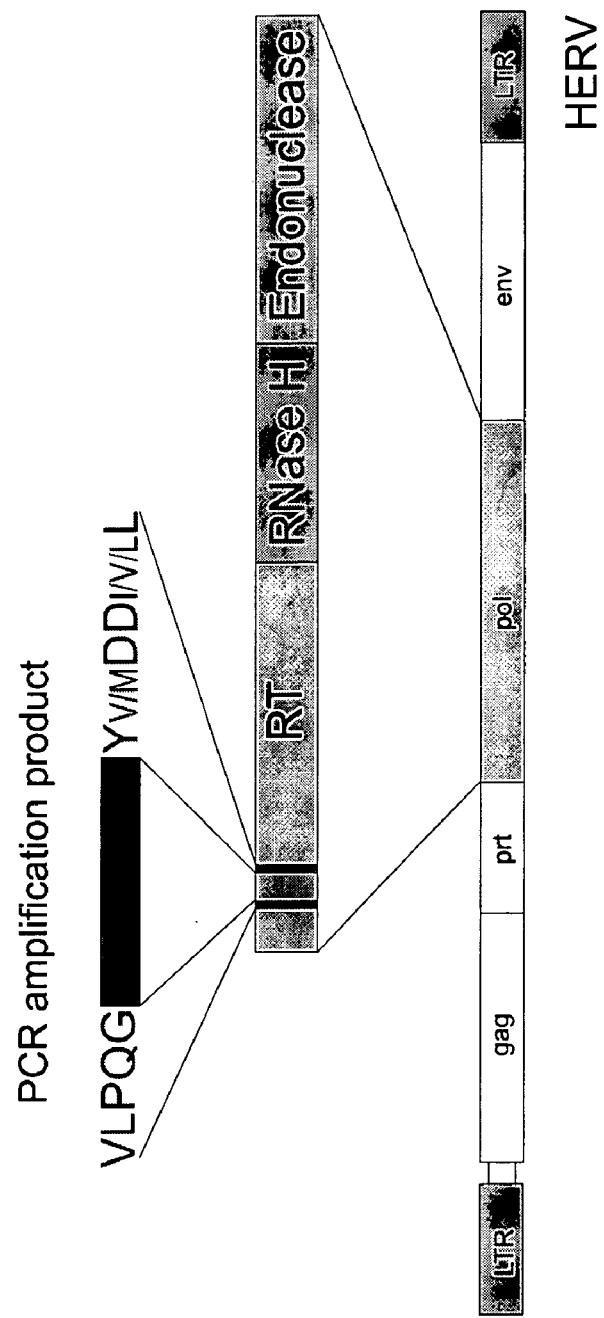
FIG. 1 Localisation of conserved amino acid sections in the amino-terminal gene regions of the reverse transcriptase of retroviruses and retrotransposons. The core homology regions V L P Q G and Y M/V D D I/V/L L were used to derive and prepare the degenerated oligonucleotides of the primer mixtures according to the invention (MOP-ABD or MOP-C).

These primer nucleotide sequences correspond to the highly conserved core homology regions V L P Q G and Y M/V D D I/V/L L within the reverse transcriptase (RT) gene of all known endogenous and exogenous retroviruses (see FIG. 1 and the publications of Xiong and Eickbush 1990, Shih et al. 1989 and Donehower et al. 1990). The beginning of the primer nucleotide sequence at the 5' end of the appropriate retrovirus-specific core-homology region, called the "head", namely the nucleotide series GAAGGATCC is an extension sequence which consists of the so-called "clamp" sequence GAA and the BamHI restriction site GGATCC.

Instead of the "clamp" sequence described here and the BamHI restriction site described here, another "clamp" sequence and/or another interface for a restriction enzyme can also be used to produce the "head" or extension sequence of the appropriate primer. Basically however the length of this "head" or extension sequence should not be more that half the total primer length.

The MOP-ABD primer mixture allows the separate amplification of types A, B and D retrovirus and the MOP-C primer mixture allows the separate amplification of type C retrovirus. Both primer mixtures can easily be combined and thus make it possible to amplify all retrovirus types (A, B, C, and D).

EXAMPLE 3

Preparation of Probes for Reverse Dot Blot Hybridisation (RDBH)

Amino acid sequence comparisons have shown that the coding genes of all retrovirus for the reverse transcriptase and most retroelements exhibit highly conserved core homology regions (Poch et al. 1989, Shih et al. 1989, McClure 1993, Donehower et al. 1990, Xiong and Eickbush 1990). Two of the most conserved amino acid sequence sections are the amino acid motifs V L P Q G and Y Y/M D D I/V/L L (FIG. 1). The sequence region between these motifs comprises approximately 90 base pairs (i.e. is approximately 90 bp long) and exhibits a significantly lower homology within the various retrovirus families. This region was used to prepare retrovirus-specific probes for RDBH.

Here the following procedure was adopted: first, generally accessible nucleotide sequence data banks were searched for nucleotide sequences related to the nucleotide sequence of the reverse transcriptase (RT). Sequences of exogenous and endogenous retroviruses were classified according to the valid nomenclature and subclassified into subclasses in terms of their RT homology (data not shown here). Some as yet unpublished HERV sequence data were kindly made available by Martin Herrmann (1998) and some were characterised by ourselves. Representative members were selected from all known retrovirus families (Table 3) and in each case an approximately 90 bp long fragment was isolated from their respective RT gene, in each case in the region between the highly conserved RT motifs V L P Q G and Y M/V D D I/V/L L, and was used as a template for synthesising the corresponding RDBH probes. Since the efficiency of an oligonucleotide synthesis decreases with the length of the oligonucleotide to be synthesised, instead of a 90 pb long oligonucleotide (90-mer) two 45 bp long oligonucleotides (45-mers) were synthesised in each case and used as a pair. Each dot (spot) of the dot blot prepared as described here corresponds to an equimolar mixture of equal proportions of one pair of 45-mers from the group of pairs listed in Table 2.

EXAMPLE 4

Preparation of Reverse Dot Blot Membranes for RDBH

Retrovirus-specific oligonucleotides which correspond to a 90 bp long fragment of the highly conserved domains of the RT gene were synthesised and purified by HPLC. For each retroviral nucleotide sequence to be tested equimolar quantities of both partners of a pair of 45-mer oligonucleotides prepared as in example 3 were mixed together and 100 picomole of this pair mixture was dissolved in 5×SSC (1×SSC=0.15M NaCl plus 0.015 M sodium citrate) and then dropped manually or by machine onto a commercially available filter membrane (for example, a ZETAprobe™ GT blotting membrane supplied by BioRad, Hercules Calif. USA) using a commercially available dot blot apparatus (for example, Minifold I dot blotter SRC96D made by Schleicher & Schuell, Dassel, Germany). The filters were equilibrated in 2×SSC, the oligonucleotides were irreversibly immobilised, preferably by means of UV cross linking (for example, using the commercially available UV emitter Stratalinker™ supplied by Stratagene, La Jolla, Calif. USA) and the filters were then dried in air.

After the amplificate DNA has been hybridised to the RDBH probes covalently linked to the membranes, bound amplificate DNA can be re-dissolved from the dot blot membrane by alkaline denaturation and if necessary re-amplified to achieve sufficient quantities of double-strand DNA, e.g. for cloning and subsequent sequence analysis of the amplificates concerned.

EXAMPLE 5

Reverse Transcription and Polymerase Chain Reaction (RT-PCR)

From each test formulation 500 ng of DNA-free mRNA were reverse transcribed at 37° C. for 1 hour in 50 µl of a solution of 20 mM pH 8.4 tris/HCl, 10 mM dithiothreitol (DTT), 50 mM KCl, 2.5 mM MgCl$_2$, 0.5 mM of each desoxynucleoside triphosphate (dNTP), 10 units of RNasin (Promega) 30 pmol Random hexamer oligonucleotides (Promega) and 20 units of MLV reverse transcriptase (GIBCO-BRL).

The formulations were then denatured, for example by heat treatment at 95° C. for 5 min and stored at −20° C. before further usage.

For the MOP-PCRs according to the invention (with MOP-ABD and/or MOP-C) in each case a volume of one twentieth (1/20) of the cDNA reaction was amplified in 50 µl of a solution of 10 mM pH 8.3 tris/HCl, 50 mM KCl, 2.5 mM $MgCl_2$, 0.001% gelatine, 50 pmoles of the relevant primer mixture(s) of degenerated oligonucleotides according to the invention, 0.25 mM of each desoyxnucleoside triphosphate and 1.25 units Taq polymerase (GIBCO-BRL). The test formulations were prepared on ice and coated with 50 µl of mineral oil (Sigma). Amplification was carried out in a commercially available DNA thermal cycler (for example supplied by Perkin Elmer Cetus) using the "Hot-Start method" familiar to the specialist whereby 30 cycles were run through, each having the following parameters: 30 sec at 94° C., 4 min at 50° C. and 1 min at 72° C. Finally an extension step was carried out at 72° C. for 7 min. The annealing time, i.e. the time taken for double strand formation, was 4 minutes in order to ensure that the vast majority of the primers (degenerated oligonucleotides) contained in the primer mixture according to the invention find the matrices homologous to them. The extension sequence of the primer according to the invention has a stabilising effect on the primer matrix binding kinetics so that the PCR products formed in the first PCR cycle are amplified significantly more efficiently in the following cycles. There is thus the advantage that retroviral matrices are (can be) then amplified themselves if the exactly matching primer is not present in the primer mixture according to the invention. In addition, it is possible to achieve fast cloning of the amplification products e.g. for a sequence examination or to characterise new RT-related nucleotide sequences.

The reaction conditions for the PCR were optimised with respect to the amount of primer, the annealing time (double strand formation time) and the annealing temperature (double strand formation temperature) in order to achieve an optimum product yield.

In order to detect product contamination from previous PCR experiments and any traces of genomic DNA contaminations in the solutions used, a control reaction was carried out in which the matrices were omitted. The amplification products were separated electrophoretically on preparative 2.5% TBE agarose gels and stained with ethydium bromide. Bands of between 100 and 150 bp which corresponded to the amplified retroviral RT nucleotide sequences were cut from the gel and cleaned using a commercially available cleaning set (for example, the GENECLEAN II kit from BIO 101 Inc., Vista Calif. USA). For the RDBH approximately 50 ng of the cleaned fragment was labelled with [α-$^{32}$P]dATP (3000 Ci/mmol). The labelling was carried out using a Megaprime DNA labelling kit (Amersham Pharmacia Biotech, England) but can also be carried out equally well using other common labelling methods.

EXAMPLE 6

Reverse Dot Blot Hybridisation (RDBH)

The RDBH method was used both to detect and to identify the amplified products. This RDBH method can strictly discriminate (distinguish) PCR products so that any wrongly amplified nucleotide sequences which are not related to nucleotide sequences of retroviral RT genes are of no importance. The high stringency of the RDBH is achieved by using synthetic HERV-specific oligonucleotides according to the invention which are applied as RDBH probes onto the dot blot filter membrane. The important advantage of these RDBH probe oligonucleotides according to the invention is that they contain none of the nucleotide sequences which are exhibited by the degenerated oligonucleotides of the MOP-ABD and MOP-C PRC primer mixtures according to the invention (see, for example, Table 1) and thus differ fundamentally from these PCR primer oligonucleotides. This fundamental difference between the RDBH probe oligonucleotides and the PCR primer oligonucleotides ensures that a hybridisation between an RDBH probe and a PCR amplificate only takes place if the nucleotide sequence between the two primers corresponds to the relevant RDBH probe oligonucleotide, i.e. if this nucleotide sequence is identical to the relevant RT nucleotide sequence section or only differs in a few nucleotides (n=3). In the ideal case the hybridising DNA sequences should be completely identical. In practice, under the given hybridisation conditions differences of two to three nucleotides are tolerable. Consequently, under highly stringent conditions even closely related retroviral nucleotide sequences can be distinguished from one another and be uniquely identified.

In order to avoid cross hybridisations, the optimum stringency conditions for the RDBH were determined by varying hybridisation temperature, washing temperature and salt concentrations. Pre-hybridisation of the reverse D blot filters was carried out in heat-sealed plastic pockets in 0.25 M pH 7.2 $Na_2HPO_4$, 7% sodium dodecylsulphate (SDS), 1 mM EDTA at 50° C. for at least 3 hours. For the actual hybridisation these solutions were mixed with $5 \times 10^5$ CpM of the labelled PCR amplificate per ml hybridisation volume and incubated for 16 hours under the same conditions. The membranes were then washed twice in 40 mM pH 7.2 $Na_2HPO_4$, 5% SDS, 1 mM EDTA and twice in 40 mM $Na_2HPO_4$ pH 7.2, 1% SDS, 1 mM EDTA (for approximately 30 min in each case). The reaction was studied and evaluated by autoradiography.

EXAMPLE 7

Figure 2:
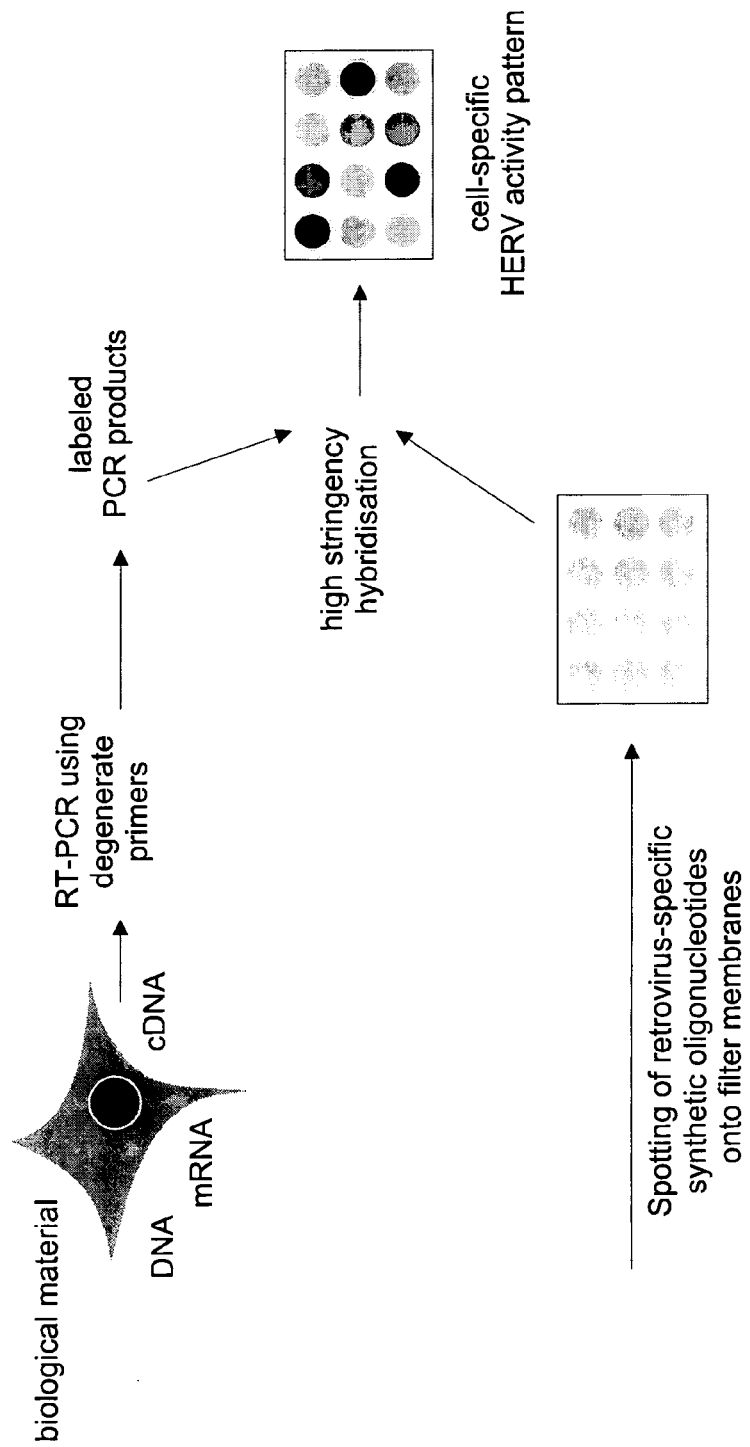
FIG. 2. Schematic of the RT-PCR/RDBH method according to the invention.
Figure 3:
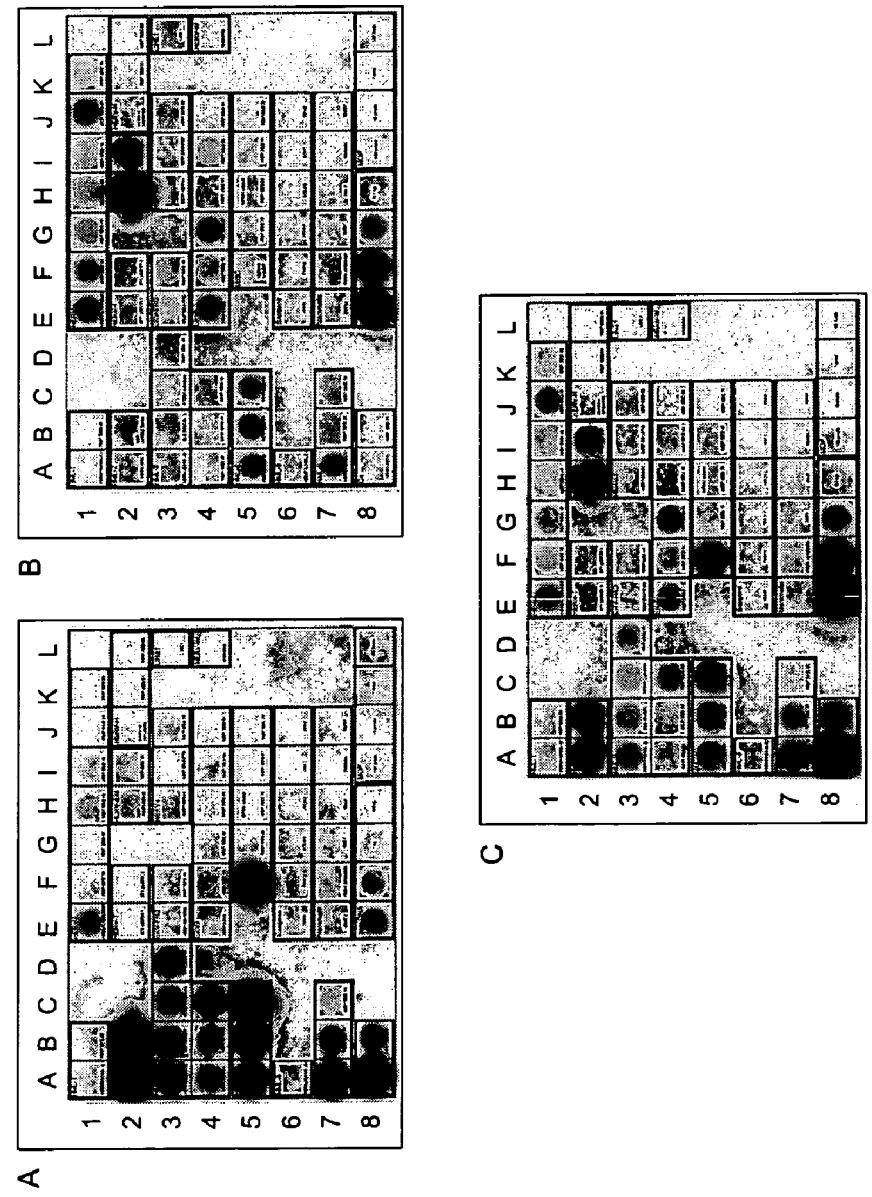
FIG. 3. HERV expression pattern in human PBMNCs of a healthy blood donor.

Analysis of the HERV Transcription Pattern in Human PBMNCs Using the PCR/RDBH Method According to the Invention First, using the method shown in FIG. 2, total RNA was extracted from human PBMNCs as in Example 1 using common isolation techniques. This total RNA was first subjected to an RT-PCR/RDBH using the MOP-ABD primer mixture according to the invention. Here almost exclusively type B-related HERVs, i.e. members of the HERV-K superfamily were detected (FIG. 3A). The most transcripts originated from members of the HERV-K subgroups HML-2, -3, -4 and -6. Also found were signals from HERV-KC4 related elements (8A, 8B) and from another HERV-K related nucleotide sequence which could not be assigned to any of the HML subgroups (5F). The observed expression pattern agrees with the studies already published which established a differentiated expression of HML elements in human tissue in the result (Medstrand et al. 1993, Andersson et al. 1996). Also found were small quantities of the element HERV-L related to the human foamy virus whereby the high specificity of the MOP-ABD primer mixture for type ABD related elements is shown.

At the same time as this test the total RNA from PBMNCs was subjected to an RT-PCR/RDBH using the MOP-C primer mixture according to the invention. Unlike the MOP-ABD primer mixture, the MOP-C primer mixture is not only suitable for priming type-C related nucleotide sequences but also amplifies HERV-K related elements of the HML-2, HML-4 and HML-6 subgroups. A strong expression of HERV-E4-1 related elements (2H and 21), human foamy virus related HERV-L elements (1E to 1K) and ERV9 related HERVs (4E to 4G and 4I) could be detected. Although the same quantities of radioactively labelled PCR-amplificates were used in all RDBH reactions, the genomic DNA probes present on the membranes (8E to 8H) after hybridisation using MOP-C produced PCR amplificates yielded significantly stronger signals than after hybridisation using MOP-ABD produced PCR amplificates. These findings indicate that the human genome contains significantly more copies of type C related HERV elements than type B related HERV elements.

In order to detect all retroviral nucleotide sequences in a single experiment the MOP-ABD and MOP-C primer mixtures were used in a combination of equimolar quantities in a PCR/RDBH method according to the invention. This experiment resulted in a predominant amplification of type C related nucleotide sequences whereas the ABD type sequences remained underrepresented (data not given here). For this reason separate PCR methods were carried out using first MOP-ABD primer mixtures and second MOP-C primer mixtures and the purified amplification products of both methods were combined in equal quantities. The RDBH was then carried out using this combination of amplification products. The signal pattern shown in FIG. 3C was obtained which corresponds to the theoretical combination of the signal pattern of the RDBH method using MOP-ABD amplificates as in FIG. 3A on the one hand and using MOP-C amplificates as in FIG. 3B on the other hand. This finding shows that the PCR/RDBH method according to the invention is overwhelmingly well suited especially as a qualitative method of detection.

EXAMPLE 8

Proof of the Sensitivity of the PCR/RDBH Method According to the Invention

In order to check the sensitivity of the PCR/RDBH method according to the invention with reference to the desired practical application in routine diagnostics e.g. to detect or eliminate any interspecies transmission of PERV with xenotransplants, dilution series experiments were carried out using cDNA from human PBMNCs and decreasing concentrations of a cloned DNA fragment that contains a PERV RT-coding region (Takeuchi et al. 1998). Under standardised test conditions even such a small quantity as 10 copies of PERV DNA could be detected in cDNA obtained from 25 ng human PBMNC mRNA (see FIG. 4A, Filter code 7F).

No cross hybridisations between human specific amplificates and PERV specific RDBH probes were observed (see FIG. 3C, filter code 7F). Even when the PCR/RDBH method was carried out using pure porcine DNA as PCR matrix (FIG. 4B), no cross hybridisations could be detected between the porcine amplificates and the human endogenous or exogenous retroviral nucleotide sequences. These results are a very strong indication of the very high interspecies specificity of the PCR/RDBH method according to the invention.

The results obtained in the test described here, namely the weak signal obtained with the murine type C retrovirus specific probe (7 I) surprisingly indicate that the porcine genome DNA also contains PERVs homologous to MoMuLV. Further results of this test, namely the observation of a weak signal with human DNA probes (8E, 8F) also surprisingly indicate that even the human genome possibly contains PERV related nucleotide sequences which have no counterpart on the dot blot membrane used and consequently are probably still uncharacterised. These findings clarify the extraordinary advantage of the PCR/RDBH method according to the invention, namely that it is possible to find, isolate and clone as yet unknown DNA fragments.

TABLE 1

| primer | nucleotide sequence | degeneration |
|---|---|---|
| MOP-ABD | forward-<br>GAAGGATCCARAGTNYTDYCHCMRGGH | 3456 |
| | reverse-<br>GAAGGATCCNWDDMKDTYATCMAYRWA | 27648 |
| MOP-C | forward-<br>GAAGGATCCTKKAMMSKVYTRCYHCARGGG | 3072 |
| | reverse-<br>GAAGGATCCMDVHDRBMDKYMAYVYAHKKA | 8192 |

TABLE 2

| Code | Source | Probe | Oligonucleotide sequence (5' -> 3') |
|---|---|---|---|
| 1A | U35102, Medstrand et al. 1993 | HML-1 | ATGCTAAATAGCCCAACTGTTTGTTAAACTTATGTCAGAAAG<br>ATGTTAAATAGCCCAACTATTTGTCAAACCTATGTTGGGAAA |
| 1B | S77579, Levebvre et al. 1995 | SEQ29 | ATGTTAAATAGCCCAACTATTTGTCAAACCTATGTTGGGAAA<br>ATTAAGCCAGTTAGAGAACAGTTTTAAAAATGTTATAGTATT |
| 1E | G895836, Cordonnier et al. 1995 | HERV-L | TATATCAACTCTCCGGCTTTGTGTCATAATCTTATTCAGAGT<br>CTTGATCACTTTTCACTGCCACAAGATATCACACTGGTCCAT |
| 1F | Herrmann 1998 | SEQ39 | GTATATCAACTCTCCAGCTTTGTGTCATCATCTTATTCAGAG<br>CCTTGATCACTTTTCACTTCTGCAAGATATCATGCTGGTCCA |
| 1G | Herrmann 1998 | SEQ40 | TTAATCAACTCTCTAGCTTTGTATCATAATCTTATTCGGAGA<br>CCTGATCGCTTTTCGCTTCCGCAAGATATCACACTGGGTTT |
| 1H | Herrmann 1998 | SEQ45 | TATATCAGTTATCTGGCTTTGTGACGTAATCTTATTTGGAGA<br>CTAGATAACTTTTCACTTCCACAAGATATCACACTGGTCCAC |

TABLE 2-continued

| Code | Source | Probe | Oligonucleotide sequence (5' -> 3') |
|---|---|---|---|
| 1I | Herrmann 1998 | SEQ48 | TATATCAACTCTCCAGCTTGTGTTATAATTTTATTCAGAGAG TTGATCACTTTTTGCTTCCACAAGATATCACACTGATTGCCT |
| 1J | Herrmann 1998 | SEQ51 | TGTATCAACTCTCTGGCTTTGTGTCATAATCTTACCTGGAGA CTTGATCGCTTTTTGCTTCCACNAGATATCACACTGGTCCAT |
| 1K | Herrmann 1998 | SEQ58 | TATATCAACTCTCCAGTTTTGTGTCATAGTCTTAGTCAGAGA CTTGATCACTTTTTGCTTCCATAAGACATCACACTGGCCCAT |
| 2A | M14123 Ono et al. 1986 | HERV-K10 | ATGCTTAATAGTCCAACTATTTGTCAGACTTTTGTAGGTCGA CTTCAACCAGTGAGAGAAAAGTTTTCAGACTGTTATATTATT |
| 2B | U87592 Zsiros et al.. 1998 | SEQ U87592 | ATGCTTAATAGTCCAACTATTTGTCAGACTTTTGTAGGTCGA CTTCAACCAGTTAGAGAAAAGTTTTCAGACTGTTATATCATT |
| 2E | U12970 Haltmeier et al. 1995 | pCRTK1 | TTTAAAAACTCCCCTACCCTTTTTGGGGAAGCCCTCCAACA CTTATACCATTCTGAGCCAGTAACCCTCACTGCACTCTTCTC G |
| 2F | U12969 Haltmeier et al. 1995 | pCRTK6 | TTTAAAAATTCCGCCACCCTTTTTGGGGAAGCCCTCCAACA CTTCTACCATTCTGAGCCAGTCCCCTTAACTGTAACTCTTCT |
| 2H | M10976 Repaske et al. 1985 | HERVE41 | TTCAAGAACTCCCCCACCATCTTTGGGGAGGCGTTGGCTCG CCTCCAGAAGTTTCCCACCAGAGACCTAGGCTGCGTGTTGC C |
| 2I | Herrmann 1998 | SEQ32 | TTCAAGAACTCCCTTACTATCTTCGGGGAGGCTCTGACTTG TTGCAAAAGTTTCCTGCTAAAGACCTAGGCTATGTCTTGCTC G |
| 2J | AF026252, Lindeskog et al. 1998 | HERV-H | TTCACAGACAGCCCCCATTACTTCAGTCAAGCCCAAATTTCT TTATCTGTTACCTATCTCCGCATAATTCTCATAAAAACACAC |
| 2K | Herrmann 1998 | SEQ61 | TTCAGAGACAGCCCCCATTACTTTAGTCAAGCTCTTTCTCAT CTACTTTCTTTCCATCCATCTGTTTCTCACCTTATTCAATAC |
| 2L | Herrmann 1998 | SEQ66 | TTCAGAGACAGCCCCCATTACTTTAGTCAAGCTCTTTCTCAT CTACTTTCTTTCCATCCATCTGTTTCTCACCTTATTCAATATA |
| 3A | U35236, Medstrand et al. 1993 | HML-3 | ATGTTAAACAGTCCAACAATTTGCCAGACTTATATGGGCAAG TTGAACCTACTCTTAAAAAATTTTCACAGTGTTACATTATTCA |
| 3B | S66676, Kalden und Herrmann, 1993 | HERV1 SLE | ATGATAAACAGTCCAACAATTTGCCAGGCATATGTAGGGCA AAWTGAACCTACYTGTAAAAAATTTTCAGTGTTACATTATTC |
| 3C | S77583 Lefebvre et al. 1995 | RT244 | ATGTTAAACAGTCCCACAATTTGCCAGTCATATGTGGGCCA ATTGAACCTACTCCTAAAAAATTTTCACAGTGTTACATTATTC |
| 3D | Herrmann 1998 | SEQ26 | CGTGTTAAACAGTCCGACTATTTGCCAGAAGTATGTGGGGG CAATTGAATCTACTCGTAAAAAATTTTCACAGTGTTACATTAT |
| 3E | U27240 Seifarth et al. 1995 | ERV-FRD | TTCAGAGATAGTCCCCATTTGTTTGGGCAAGCCTTGGCTAG TTTGCAGGACCTAAGTCTTTATATGGAAGGGCATCTCCTAC |
| 3F | Herrmann 1998 | SEQ46 | TTCAGAGATAGTCCCCATTTGTTTGGCAAGCCTTGGCTAGA TGCAGGACCTAAGTCTTTATATGGGAGGGCATCTCCTACAG A |
| 3H | M92067 Maeda and Kim 1990 | HERV-I | TTCATGGATTCACCCAACCTTTTTGGTCAAATTTTAGAACAA CTAGACAAAGTTTCTGTTCCAAAACAATTATGCCTGCTTCAA |
| 3I | U27241 Seifarth et al. 1995 | HERV-IP (T47D) | TTCACAGACTCCCCTAATATTTTTGGTGAAATTTTAGAACAA ATTAGAAAAGTTTTCATTCCAGAACAAATATGCCTTCTCCA |
| 3J | Herrmann 1998 | SEQ65 | AGACTCCCCTAATCTTTTTGGCCAAATTTTAGAACAAGTGTT AAAAGTGGTCATCCCAAAGCAAATATGCTTGCTCTAGTACA |

TABLE 2-continued

| Code | Source | Probe | Oligonucleotide sequence (5' -> 3') |
|------|--------|-------|-------------------------------------|
| 3L | McMillan and Singer 1993, M80343 | LINE-I | TGCCCTCTCTCACCACTCCTATTCAACATAGTGTTGGAAGTT GCCAGGGCAATTAGGCAGGAGAAGGAAATAAAGGGTATTC |
| 4A | Herrmann 1998 | SEQ34 | ATGTTAAATGGTCCCACAATTTGCCAGACATATGTGGGGCA CTTGAACTTACTCATAAAAAATTTTCAGTGTTACATTATTCAC |
| 4B | Herrmann 1998 | SEQ42 | ATGTTAAACTGTCCAACAATTTGTCAGACTTATGTAGAACAA ATTGAACCTACTCATAAAAAATTTTCAGTGTTATATTATTCAT |
| 4C | Herrmann 1998 | SEQ43 | ATGTTAAACAGTCCAACAATTTGCCAGATGTACGTGGTGCA AATTGAACCTACTTGTAAAAAATTTTTGGTGTTACATTNTTCN |
| 4E | X57147, La Mantia et al. 1991 | ERV9 | TTTAGGGATAGCCCTCATCTGTTTGGTCAGGCCCTAGCCAA GATCTAGGCCACTTCTCAAGTCCAGGCACTCTGGTCCTTCA |
| 4F | Herrmann 1998 | SEQ49 | TTCAGGGATATAGCCCCCATCTATTTGGTCAGGCATTAGCC CTTGAGCCAGTTCTCATACCTGGACACTCTGGTCCCTTTGG A |
| 4G | Herrmann 1998 | SEQ59 | TTTAGGGATAGCCCTCATCTGTTTGGTCAGGCACAGGCCCA ATCTAGTTCACTTCTCAAGTCCAGGCACTCTGGTTGTTCAGT |
| 4H | Herrmann 1998 | SEQ60 | TTTAGGGACAGCCCTCACTATTTCGGTCAGGCACTTCAATT ACCTCTCCCAGCTACATCTNCNNCCYNGCATCTTGCTTCAG |
| 4I | Herrmann 1998 | SEQ63 | TTCAGGGATAGCTCCCATCTATTTGGCCAGGCATTAACCCG ACTTAAGCCAGTTCTCATACGTGGACACTCTTGTCCTTTGGT |
| 4J | Herrmann 1998 | SEQ64 | TTTAGAGATAGCCCTCACCTGTTTGGCCAAGCATTGGCCAA TTTAAGTCACTTCTTGCACCCAGGTACCCTAATTCTTCAATA |
| 4L | AF009668 Blond et al. 1999 | HERV-W | TTCAGGGATAGCCCCCATCTATTTGGCCAGGCATTAGCCCA ACTTGAGTCAATTCTCATACCTGGACACTCTTGTCCTTCAGT |
| 5A | AF020092 Seifarth et al. 1995 | HERV-K (T47D) | CATGCTTAATAGTCCCACTATTTGTCAGTATTTTGTGGGGCG GCTTCAACCTGTCAGGGATCAGTTTCCCCGATGTTACATCG |
| 5B | Herrmann 1998 | SEQ05 | ATGCTTAATAGTCCCACTATTTGTCAGTATTTTGTGGGGCGT CTTCAACCTGTCAGGGATCAGTTTCCCCGATGTTACATCGT |
| 5C | Herrmann 1998 | SEQ10 | ATGCTTAATAGTCCCACTATTTGTCAGTATTTTGTGGGGTG TTCAACCTGTCAGGGATTCAGTTTCCCCGATGTTACATCGTT |
| 5E | U46939 Griffiths et al. 1997 | SEQ U46939 | ATGACTAACAGTCCTGCCATATGCCAGCTATATGTTGACCA GTAGAGCCTGTTCGGCAGCAGTGCCCAAAAGTACAAATTTT |
| 5F | U39937 Li et al. 1995 | U39937 | ATGCTTAATAGTCCAACTATTTGTCAGACTTTTGTAGGTCGA CTTCAACCAGTTAGAGAAAAGTTTTCAGACTGTTATATTATT |
| 5G | Herrmann 1998 | SEQ35 | AACCAGTATCAGGAGTTTTACAGCCAGGTAGTCAGGAGGAA AGTCATCCTGGTGCAGTGGAAAGGGCATTGGATTTAAAGGC CT |
| 5H | Herrmann 1998 | SEQ36 | AACAATGTTAGAATGGCTCACAGAACTCAGGAAAATACTTTA GTATTTAATGGTTTGTTACATAAGATACAACTCAAGGAACCA |
| 5I | Herrmann 1998 | SEQ41 | TACCATGGACGACAAGCCTTCGTGTTACCACAAGGCACTGC G CAAGCATTGAATGTGATCGTTTGAGGGCAGGGTGATCGGG A |

TABLE 2-continued

| Code | Source | Probe | Oligonucleotide sequence (5' -> 3') |
|---|---|---|---|
| 5J | Herrmann 1998 | SEQ77 | TGGAAGGGAGGACTTGAGCACATTCTTAAATGT GGCTCCTGTAATTTTTAACACATTGACACATGCTA |
| 6A | U35161 Medstrand et al. 1993 | HML-5 | ATGCTGAACAGTCCTACCATGTGTCAGTAACATGTAAATCAA TTGCTCCCCAGTAGAAAATAATTTCCTAATTGCAAGATTATT |
| 6E | HRU46939 Griffiths et al. 1997 | HRV5 | ATGACTAACAGTCCTGCCATATGCCAGCTATATGTTGACCA GTAGAGCCTGTTCGGCAGCAGTGCCCAAAAGTACAAATTTT |
| 6F | Y07725 | Foamy virus | TTTTTAAATAGTCCAGCATTGTTTACAGCTGATGTAGTAGAT CTAAAAGAAATCCCTAATGTACAAGTGTATGTTGATGATATA |
| 6G | Tuke et al. 1997 | HTLV1 | GTTTAAAAATAGTCCCACCCTGTTCGAAATGCAGCTGGCCC CCTGCAGCCCATTCGGCAAGCTTTCCCCCAATGCACTATTC |
| 6H | M10060, Shimotohno et al. 1985 | HTLV2 | GTTTAAAAACAGCCCCACCCTCTTCGAACAACAATTAGCAG CCTCAACCCCATGAGGAAAATGTTTCCCACATCGACCATTG |
| 6I | Tuke et al. 1997 | HIV1 | ATGGAAAGGATCACCAGCAATATTCCAAAGTAGCATGACAA CTTAGAGCCTTTTAAAAAACAAAATCCAGACATAGTTATCTA |
| 6J | J04542 | HIV2 | TGGAAAGGATCACCAGCAATCTTTCAATTCATGATGAGGCA TTAGAACCTTTCAGAAAAGCAAACCCAGACGTCATTCTCATC |
| 7A | U60269 Medstrand et al. 1997 | HML-6 | ATGCTTAACAGTCTTACGCTATGTCAGCATTTTGTAGGACAG TTAAAGAAGCCTCGGAATATGTTTCCTACTGCTTACATCATT |
| 7B | Herrmann 1998 | SEQ38 | ATGCTCAACACCTACGTTAAGTCAGCATTTTGTAGGAAGAG T AAAGGACTCTCAGAATATGTTTCCCACTGCCTACATCGTTCA |
| 7C | Herrmann 1998 | SEQ56 | ATGCTTAACAGCATTATATCAGCATGTTGTAGGATAGGCAT TAAA GGTGCCTCTGAATATGTTTCCCACAGCCTACATCCGTCATT T |
| 7E | M15122 Moore et al. 1987 | MMTV | ATGAAAAATAGCCCTACTTTATGTCAAAAATTTGTGGACAAA ATATTGACTGTAAGGGATAAATACCAAGACTCATATATTGTG |
| 7F | AF038600 Akiyoshi et al. 1998 | PERV | TTCAAGAACTCCCCGACCATCTTTGACGAAGCCCTACACAG CTGGCCAACTTCAGGATCCAACACCCTCAGGTGACCCTCCT G |
| 7G | D10032 Kato et al. 1987 | BaEV | TTCAAAAACTCTCCCACTCTCTTCGATGAGGCTCTCCACAG CTCACCGACTTCCGGACCCAGCATCCAGAAGTGACCCTGC G |
| 7H | M26927 Delassus et al. 1989 | GaLV | TTCAAGAACTCTCCCACTCTCTTCGACGAGGCCCTCCACCG TTGGCTCCCTTTAGGGCCCTCAACCCCCAGGTGGTGTTACT |

TABLE 2-continued

| Code | Source | Probe | Oligonucleotide sequence (5' -> 3') |
|---|---|---|---|
| 7I | J02255 Van Beveren et al. 1981 | MoMuLV | TTCAAAAACAGTCCCACCCTGTTTGATGAGGCACTGCACAG<br>CTAGCAGACTTCCGGATCCAGCACCCAGACTTGATCCTGCT |
| 7J | M12349 Sonigo et al. 1986 | MPMV | ATGGCCAACAGTCCTACCTTATGTCAAAAATATGTGGCCAC<br>ATACATAAGGTTAGACATGCCTGGAAACAAATGTATATTATA |
| 8A | U07856, Dangel et al. 1994 | HERV-KC4 | ATGTTAAATAGTCCCACAGTTTGTCAAACTTTTGTAGGCAGA<br>ATCCAGCCTGTTAGAGATCAGTTTCCAGATTTGTCAGCAA |
| 8B | Herrmann 1998 | SEQ31 | ATGTTAAACAGTTCCACAGTTTGTCAAACTTTTGTAGGCAAA<br>ATCCAGCTAGTTAGAGATCAATTTCCAGATTGTTACATCATT |
| 8E–8H | human genomic DNA | internal control | 100 ng<br>10 ng<br>1 ng<br>0.1 ng |
| 8I–8L | mixed oligo primers | internal control | 100 pmol<br>10 pmol<br>1 pmol<br>0.1 pmol |

TABLE 3

A. Human endogenous retroviral sequences

| | | |
|---|---|---|
| type-B retroviruses (HERV-K-superfamily) | HML-1 subgroup | HML1 (1A)<br>Seq29 (1B*) |
| | HML-2 subgroup | HERV-K10 (2A)<br>U87592 (2B) |
| | HML-3 subgroup | HML-3 (3A)<br>S66676 (3B*)<br>RT244 (3C*)<br>Seq26 (3D*)<br>Seq34 (4A*)<br>Seq42 (4B*)<br>Seq43 (4C*) |
| | HML-4 subgroup | HERV-K-T47D (5A)<br>Seq05 (5B)<br>Seq10 (5C) |
| | HML-5 subgroup | HML-5 (6A) |
| | HML-6 subgroup | HML-6 (7A)<br>Seq38 (7B)<br>Seq56 (7C) |
| | KC4 subgroup | HERV-K-C4 (8A)<br>Seq31 (8B) |
| | not defined | U39937 (5F) |
| type-C retroviruses | HERV-H & related | AF026252 (2J)<br>Seq61 (2K)<br>Seq66 (2L) |
| | ERV9 & related | ERV9 (4E)<br>Seq49 (4F)<br>Seq59 (4G)<br>Seq60 (4H)<br>Seq63 (4I)<br>Seq64 (4J) |
| | ERV-FRD | ERV-FRD (3E)<br>Seq46 (3F) |
| | HERV-ERI family | HERV-E(4-1) (2H)<br>Seq32 (2I) |
| | HERV-I & related | HERV-I (3H)<br>HERV-IP-T47D (3I)<br>Seq65 (3J) |
| | HERV-T | S71 pCRTK1 (2E)<br>S71 pCRTK2 (2F) |
| | HERV-W | AF009668 (4L) |
| type-D retroviruses | MPMV related | Seq36 (5H) |
| Foamy virus related | HERV-L & related | G895836 (1E)<br>Seq39 (1F)<br>Seq40 (1G)<br>Seq45 (1H)<br>Seq48 (1I)<br>Seq51 (1J)<br>Seq58 (1K) |
| undefined retroviral elements | | U46939 (5E)<br>Seq35 (5G)<br>Seq41 (5I)<br>Seq77 (5J) |
| human non-viral retroposons | | LINE-1 (3L) |

B. Exogenous retroviruses

| | |
|---|---|
| Human exogenous retroviruses | HRV5 (6E)<br>Foamy virus (6F)<br>HTLV-1 (6G)<br>HTLV-2 (6H)<br>HIV-1 (6I)<br>HIV-2 (6J) |
| endogenous Mammalia retroviruses | MMTV (7E)<br>PERV (7F)<br>BaEV (7G)<br>GaLV (7H)<br>MoMuLV (7I)<br>MPMV (7J) |

What is claimed is:

1. A MOP primer mixture of oligonucleotides which are forward and reverse primers for PCR comprising: at least one of MOP-ABD or MOP-C and wherein MOP-ABD consists of a forward primer with a head at its 5' end and a nucleotide sequence in accordance with SEQ. ID NO. 1 with 3456 degenerations, and a reverse primer with a head at its 5' end and a nucleotide sequence in accordance with SEQ. ID NO.2 with 27648 degenerations; and wherein MOP-C consists of a forward primer which is a nucleotide sequence with a head at its 5' end and a nucleotide sequence in accordance with SEQ. ID NO. 3 with 3072 degenerations, and a reverse primer with a head at its 5' end and a nucleotide sequence in accordance with SEQ. ID NO. 4 with 8192 degenerations; and wherein each of the heads defines a nucleotide sequence comprising an interface for a restriction enzyme and a clamp sequence at a 5' end of the interface and which has a length not exceeding one half of a length of a complete nucleotide sequence of one of the forward or the reverse primer.

2. The primer mixture of claim 1, wherein the head has the sequence GAAGGATCC.

3. A method for specific detection and identification of a retrovirus or retroviral nucleic acid in a specimen comprising the steps of:
   isolating at least one, DNA or RNA from the specimen;
   producing respective amplificates of the DNA or RNA by subjecting said at least one isolated DNA to PCR or isolated RNA to RT-PCR by using a primer mixture of forward and reverse primers, wherein the primer mixture comprises at least one of MOP-ABD or MOP-C and wherein MOP-ABD consists of a forward primer with a head at its 5' end and a nucleotide sequence in accordance with SEQ. ID NO. 1 with 3456 degenerations, and a reverse primer with a head at its 5' end and a nucleotide sequence in accordance with SEQ. ID NO.2 with 27648 degenerations; and wherein MOP-C, consists of a forward primer which is a nucleotide sequence with a head at its 5' end and a nucleotide sequence in accordance with SEQ. ID NO. 3 with 3072 degenerations, and a reverse primer with a head at its 5' end and a nucleotide sequence in accordance with SEQ. ID NO. 4 with 8192 degenerations; and wherein each of the heads defines a nucleotide sequence comprising an interface for a restriction enzyme and a clamp sequence at a 5' end of the interface and which has a length not exceeding one half of a length of a complete nucleotide sequence of one of the forward or the reverse primer;
   purging the amplificates;
   detecting and identifying the presence of a retroviral nucleotide sequence of a retrovirus-specific reverse-transcriptase gene or a section thereof by subjecting the amplificates to reverse dot blot hybridization (RDBH) using immobilized RDBH probes, wherein each said probes includes at least one of synthetic oligonucleotide sequences corresponding to the retroviral nucleotide sequence of the retrovirus specific reverse transcriptase gene or a section thereof, and which do not overlap with nucleotide sequences of the forward and reverse primer of the primer mixture.

4. The method of claim 3, wherein each of the RDBH probes correspond to a region of the retroviral nucleic acid of the reverse transcriptase gene between highly conserved motifs V L P Q G and Y M/V D D I/V/L L, or a section of this region.

5. The method of claim 4, wherein each of the immobilized RDBH probes used is a mixture of equimolar quantities of both partners of a pair of synthetic oligonucleotides together corresponding to a section from the nucleic acid region of the reverse transcriptase gene between the highly conserved motifs V L P Q G and Y M/V D D I/V/L L.

6. The method of claim 5, wherein the section is 90 base pair long.

7. The method of claim 5, wherein both partners of the pair of synthetic oligonucleotides are approximately the same size or the same length.

8. The method of claim 7, wherein the synthetic oligonucleotides are approximately 45 base pairs long.

9. The method of claim 3, wherein the reverse dot blot hybridization probe used is at least one synthetic oligonucleotide whose nucleotide sequence corresponds with the nucleic acid region of a retrovirus-specific reverse transcriptase gene between, highly conserved motifs V L P Q G and Y M/V D D I/V/L L, or a section of this nucleic acid region.

10. The method of claim 3, wherein equimolar quantities of two synthetic oligonucleotides which together, positioned one after the other, correspond to a section from the nucleic acid region of the reverse transcriptase gene between the highly conserved motifs V L P Q G and Y M/V D D I/V/L L are used as reverse dot blot hybridization probe(s).

11. The method of claim 10, wherein the section is 90 base pairs long.

12. A diagnostic kit for the specific detection and identification of retroviral nucleic acids and/or retroviruses in an arbitrary specimen comprising:
   at least one of MOP-ABD or MOP-C and wherein MOP-ABD consists of a forward primer with a head at its 5' end and a nucleotide sequence in accordance with SEQ.

ID NO. 1 with 3456 degenerations, and a reverse primer with a head at its 5' end and a nucleotide sequence in accordance with SEQ. ID NO.2 with 27648 degenerations; and wherein MOP-C, consists of a forward primer which is a nucleotide sequence with a head at its 5' end and a nucleotide sequence in accordance with SEQ. ID NO. 3 with 3072 degenerations, and a reverse primer with a head at its 5' end and a nucleotide sequence in accordance with SEQ. ID NO. 4 with 8192 degenerations; and wherein each of the heads defines a nucleotide sequence comprising an interface for a restriction enzyme and a clamp sequence at a 5' end of the interface and which has a length not exceeding one half of a length of a complete nucleotide sequence of one of the forward or the reverse primer; and
at least one reverse dot blot hybridization probe.

13. The diagnostic kit of claim 12, wherein the reverse dot blot hybridization probe includes at least one synthetic oligonucleotide sequence which corresponds with one of a nucleic acid region of a retrovirus specific reverse transcriptase gene between highly conserved motifs V L P Q G and Y M/V D D I/V/LL or with a section thereof.

14. The diagnostic kit of claim 13, wherein the reverse dot blot hybridization probe includes at least two synthetic oligonucleotides in equimolar quantities positioned one after another and corresponding to a section of about 90 base pairs from a nucleic acid region of a reverse transcriptase gene between highly conserved motifs V L P Q G and Y M/V D D.

* * * * *

SEQUENCE LISTING

<160> NUMBER OF SEQ ID NOS: 70

<210> SEQ ID NO 1
<211> LENGTH: 18
<212> TYPE: DNA
<213> ORGANISM: Homo sapiens
<220> FEATURE:
<221> NAME/KEY: misc_feature
<222> LOCATION: (6)..(6)
<223> OTHER INFORMATION: A or C or G or T

<400> SEQUENCE: 1
aragtnytdy chcmrggh                                          18

<210> SEQ ID NO 2
<211> LENGTH: 18
<212> TYPE: DNA
<213> ORGANISM: Homo sapiens
<220> FEATURE:
<221> NAME/KEY: misc_feature
<222> LOCATION: (1)..(1)
<223> OTHER INFORMATION: A or C or G or T

<400> SEQUENCE: 2
nwddmkdtya tcmayrwa                                          18

<210> SEQ ID NO 3
<211> LENGTH: 21
<212> TYPE: DNA
<213> ORGANISM: Homo sapiens

<400> SEQUENCE: 3
tkkammskvy trcyhcargg g                                      21

<210> SEQ ID NO 4
<211> LENGTH: 21
<212> TYPE: DNA
<213> ORGANISM: Homo sapiens
<220> FEATURE:
<221> NAME/KEY: SEQID5
<222> LOCATION: (1)..(10)
<223> OTHER INFORMATION:
<220> FEATURE:
<221> NAME/KEY: misc_feature
<222> LOCATION: (1)..(10)
<223> OTHER INFORMATION:

<400> SEQUENCE: 4
mdvhdrbmdk ymayvyahkk a                                      21

<210> SEQ ID NO 5
<211> LENGTH: 9
<212> TYPE: DNA
<213> ORGANISM: artificial sequence
<220> FEATURE:
<223> OTHER INFORMATION: arbitrary head sequence
<220> FEATURE:
<221> NAME/KEY: misc_feature
<222> LOCATION: (1)..(9)
<223> OTHER INFORMATION: arbitrary head sequence

<400> SEQUENCE: 5 gaaggatcc                                                     9

<210> SEQ ID NO 6
<211> LENGTH: 90

```
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1A

<400> SEQUENCE: 6
atgctaaata gcccaactgt ttgttaaact tatgtcagaa agctaatgtt aaatagccca      60
actatttgtc aaacctatgt tgggaaagtt                                      90

<210> SEQ ID NO 7
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1B

<400> SEQUENCE: 7
atgttaaata gcccaactat ttgtcaaacc tatgttggga aagttattaa gccagttaga      60
gaacagtttt aaaaatgtta tagtattcat                                      90

<210> SEQ ID NO 8
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1E

<400> SEQUENCE: 8
tatatcaact ctccggcttt gtgtcataat cttattcaga gtgatcttga tcacttttca      60
ctgccacaag atatcacact ggtccattac                                      90

<210> SEQ ID NO 9
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1F

<400> SEQUENCE: 9
gtatatcaac tctccagctt tgtgtcatca tcttattcag agataccttg atcactttc       60 acttctgcaa gatatcatgc tggtccatta                                      90

<210> SEQ ID NO 10
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1G

<400> SEQUENCE: 10
ttaatcaact ctctagcttt gtatcataat cttattcgga gagaccctga tcgcttttcg      60
cttccgcaag atatcacact gggtttgtta                                      90

<210> SEQ ID NO 11
```

<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1H

<400> SEQUENCE: 11
tatatcagtt atctggcttt gtgacgtaat cttatttgga gagatctaga taacttttca    60
cttccacaag atatcacact ggtccactac                                     90

<210> SEQ ID NO 12
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1I

<400> SEQUENCE: 12
tatatcaact ctccagcttg tgttataatt ttattcagag agatcttgat cacttttgc     60 ttccacaaga tatcacactg attgcctaca                                     90

<210> SEQ ID NO 13
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1J

<400> SEQUENCE: 13
tgtatcaact ctctggcttt gtgtcataat cttacctgga gacatcttga tcgcttttg    60 cttccacaag atatcacact ggtccattat                                     90

<210> SEQ ID NO 14
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 1K

<400> SEQUENCE: 14
tatatcaact ctccagtttt gtgtcatagt cttagtcaga gagaccttga tcacttttg    60 cttccataag acatcacact ggcccattac                                     90

<210> SEQ ID NO 15
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 2A

<400> SEQUENCE: 15
atgcttaata gtccaactat ttgtcagact tttgtaggtc gagctcttca accagtgaga    60
gaaaagtttt cagactgtta tattattcat                                     90

```
<210> SEQ ID NO 16
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 2B

<400> SEQUENCE: 16
atgcttaata gtccaactat ttgtcagact tttgtaggtc gagctcttca accagttaga      60
gaaaagtttt cagactgtta tatcattcat                                       90

<210> SEQ ID NO 17
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 2E

<400> SEQUENCE: 17
tttaaaaact cccctaccct ttttggggaa gccctccaac aggatcttat accattctga      60
gccagtaacc ctcactgcac tcttctccag                                       90

<210> SEQ ID NO 18
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 2F

<400> SEQUENCE: 18
tttaaaaatt ccgccaccct ttttggggaa gccctccaac aagatcttct accattctga      60
gccagtcccc ttaactgtaa ctcttcttca                                       90

<210> SEQ ID NO 19
<211> LENGTH: 88
<212> TYPE: DNA
<213> ORGANISM: Homo sapiens
<220> FEATURE:
<221> NAME/KEY: misc_feature
<222> LOCATION: (1)..(88)
<223> OTHER INFORMATION: Capture probe 2F
<220> FEATURE:
<221> NAME/KEY: misc_feature
<222> LOCATION: (1)..(88)
<223> OTHER INFORMATION: Capture probe 2H

<400> SEQUENCE: 19
ttcaagaact cccccaccat ctttggggag gcgttggctc gagacctcca gaagtttccc      60
accagagacc taggctgcgt gttgctcc                                         88

<210> SEQ ID NO 20
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 2I

<400> SEQUENCE: 20
```

```
ttcaagaact cccttactat cttcggggag gctctgactt gagacttgca aaagtttcct    60
gctaaagacc taggctatgt cttgctcctg                                    90

<210> SEQ ID NO 21
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 2J

<400> SEQUENCE: 21
ttcacagaca gcccccatta cttcagtcaa gcccaaattt cttccttatc tgttacctat    60
ctccgcataa ttctcataaa aacacacgtg                                    90

<210> SEQ ID NO 22
<211> LENGTH: 87
<212> TYPE: DNA
<213> ORGANISM: Homo sapiens
<220> FEATURE:
<221> NAME/KEY: misc_feature
<222> LOCATION: (1)..(87)
<223> OTHER INFORMATION: Capture probe 2K

<400> SEQUENCE: 22
ttcagagaca gcccccatta ctttagtcaa gctctttctc atgatctact ttctttccat    60
ccatctgttt ctcaccttat tcaatac                                       87

<210> SEQ ID NO 23
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 2L

<400> SEQUENCE: 23
ttcagagaca gcccccatta ctttagtcaa gctctttctc atgatctact ttctttccat    60
ccatctgttt ctcaccttat tcaatatatg                                    90

<210> SEQ ID NO 24
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 3A

<400> SEQUENCE: 24
atgttaaaca gtccaacaat ttgccagact tatatgggca agcaattgaa cctactctta    60
aaaaattttc acagtgttac attattcatt                                    90

<210> SEQ ID NO 25
<211> LENGTH: 89
<212> TYPE: DNA
<213> ORGANISM: Homo sapiens
<220> FEATURE:
<221> NAME/KEY: misc_feature
<222> LOCATION: (1)..(89)
<223> OTHER INFORMATION: Capture probe 3B

<400> SEQUENCE: 25
```

```
atgataaaca gtccaacaat ttgccaggca tatgtagggc aaacaawtga acctacytgt      60
aaaaaatttt cagtgttaca ttattcatt                                       89

<210> SEQ ID NO 26
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 3C

<400> SEQUENCE: 26
atgttaaaca gtcccacaat ttgccagtca tatgtgggcc aagcaattga acctactcct      60
aaaaaatttt cacagtgtta cattattcac                                      90

<210> SEQ ID NO 27
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 3D

<400> SEQUENCE: 27
cgtgttaaac agtccgacta tttgccagaa gtatgtgggg gcaagcaatt gaatctactc      60
gtaaaaaatt ttcacagtgt tacattattc                                      90

<210> SEQ ID NO 28
<211> LENGTH: 87
<212> TYPE: DNA
<213> ORGANISM: Homo sapiens
<220> FEATURE:
<221> NAME/KEY: misc_feature
<222> LOCATION: (1)..(87)
<223> OTHER INFORMATION: Capture probe 3E

<400> SEQUENCE: 28
ttcagagata gtccccattt gtttgggcaa gccttggcta gatatttgca ggacctaagt      60
ctttatatgg aagggcatct cctacag                                         87

<210> SEQ ID NO 29
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 3F

<400> SEQUENCE: 29
ttcagagata gtccccattt gtttggcaag ccttggctag atatttgcag gacctaagtc      60
tttatatggg agggcatctc ctacagtaca                                      90

<210> SEQ ID NO 30
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 3H
```

```
<400> SEQUENCE: 30
ttcatggatt cacccaacct ttttggtcaa attttagaac aagtgctaga caaagtttct    60
gttccaaaac aattatgcct gcttcaatat                                     90

<210> SEQ ID NO 31
<211> LENGTH: 87
<212> TYPE: DNA
<213> ORGANISM: Homo sapiens
<220> FEATURE:
<221> NAME/KEY: misc_feature
<222> LOCATION: (1)..(87)
<223> OTHER INFORMATION: Capture probe 3I

<400> SEQUENCE: 31
ttcacagact cccctaatat ttttggtgaa attttagaac aagcattaga aaaagttttc    60
attccagaac aaatatgcct tctccag                                        87

<210> SEQ ID NO 32
<211> LENGTH: 88
<212> TYPE: DNA
<213> ORGANISM: Homo sapiens
<220> FEATURE:
<221> NAME/KEY: misc_feature
<222> LOCATION: (1)..(88)
<223> OTHER INFORMATION: Capture probe 3J

<400> SEQUENCE: 32
agactcccct aatcttttg gccaaatttt agaacaagtg ttagaaaaag tggtcatccc     60
aaagcaaata tgcttgctct agtacatg                                       88

<210> SEQ ID NO 33
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 3L

<400> SEQUENCE: 33
tgccctctct caccactcct attcaacata gtgttggaag ttctggccag ggcaattagg    60
caggagaagg aaataaaggg tattcaatta                                     90

<210> SEQ ID NO 34
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 4A

<400> SEQUENCE: 34
atgttaaatg gtcccacaat ttgccagaca tatgtggggc aagcacttga acttactcat    60 aaaaatttt cagtgttaca ttattcacta                                      90

<210> SEQ ID NO 35
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 4B
```

```
<400> SEQUENCE: 35
atgttaaact gtccaacaat ttgtcagact tatgtagaac aagcaattga acctactcat      60
aaaaaatttt cagtgttata ttattcatta                                      90

<210> SEQ ID NO 36
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 4C

<400> SEQUENCE: 36
atgttaaaca gtccaacaat ttgccagatg tacgtggtgc aagcaattga acctacttgt      60
aaaaaatttt tggtgttaca tttttctttta                                     90

<210> SEQ ID NO 37
<211> LENGTH: 84
<212> TYPE: DNA
<213> ORGANISM: Homo sapiens
<220> FEATURE:
<221> NAME/KEY: misc_feature
<222> LOCATION: (1)..(84)
<223> OTHER INFORMATION: Capture probe 4E

<400> SEQUENCE: 37
tttagggata gccctcatct gtttggtcag gccctagcca aagatctagg ccacttctca      60
agtccaggca ctctggtcct tcaa                                            84

<210> SEQ ID NO 38
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 4F

<400> SEQUENCE: 38
ttcagggata tagcccccat ctatttggtc aggcattagc caagacttga gccagttctc      60
atacctggac actctggtcc ctttggtata                                      90

<210> SEQ ID NO 39
<211> LENGTH: 87
<212> TYPE: DNA
<213> ORGANISM: Homo sapiens
<220> FEATURE:
<221> NAME/KEY: misc_feature
<222> LOCATION: (1)..(87)
<223> OTHER INFORMATION: Capture probe 4G

<400> SEQUENCE: 39
tttagggata gccctcatct gtttggtcag gcacaggccc aagatctagt tcacttctca      60
agtccaggca ctctggttgt tcagtac                                         87

<210> SEQ ID NO 40
<211> LENGTH: 86
<212> TYPE: DNA
<213> ORGANISM: Homo sapiens
<220> FEATURE:
<221> NAME/KEY: misc_feature
<222> LOCATION: (1)..(86)
```

```
<223> OTHER INFORMATION: Capture probe 4H

<400> SEQUENCE: 40
tttagggaca gccctcacta tttcggtcag gcacttcaat tagacctctc ccagctacat    60
cttcccccya gcatcttgct tcagta                                        86

<210> SEQ ID NO 41
<211> LENGTH: 86
<212> TYPE: DNA
<213> ORGANISM: Homo sapiens
<220> FEATURE:
<221> NAME/KEY: misc_feature
<222> LOCATION: (1)..(86)
<223> OTHER INFORMATION: Capture probe 4I

<400> SEQUENCE: 41
ttcagggata gctcccatct atttggccag gcattaaccc gagacttaag ccagttctca    60
tacgtggaca ctcttgtcct ttggta                                        86

<210> SEQ ID NO 42
<211> LENGTH: 86
<212> TYPE: DNA
<213> ORGANISM: Homo sapiens
<220> FEATURE:
<221> NAME/KEY: misc_feature
<222> LOCATION: (1)..(86)
<223> OTHER INFORMATION: Capture probe 4J

<400> SEQUENCE: 42
tttagagata gccctcacct gtttggccaa gcattggcca agatttaagt cacttcttgc    60
acccaggtac cctaattctt caatat                                        86

<210> SEQ ID NO 43
<211> LENGTH: 87
<212> TYPE: DNA
<213> ORGANISM: Homo sapiens
<220> FEATURE:
<221> NAME/KEY: misc_feature
<222> LOCATION: (1)..(87)
<223> OTHER INFORMATION: Capture probe 4L

<400> SEQUENCE: 43
ttcagggata gccccatct atttggccag gcattagccc aagacttgag tcaattctca     60
tacctggaca ctcttgtcct tcagtac                                       87

<210> SEQ ID NO 44
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 5A

<400> SEQUENCE: 44
catgcttaat agtcccacta tttgtcagta ttttgtgggg cgtgtgcttc aacctgtcag    60
ggatcagttt ccccgatgtt acatcgttca                                    90

<210> SEQ ID NO 45
<211> LENGTH: 90
<212> TYPE: DNA
<213> ORGANISM: Homo sapiens
<220> FEATURE:
<221> NAME/KEY: misc_feature
```

```
<222> LOCATION: (1)..(90)
<223> OTHER INFORMATION: Capture probe 5B

<400> SEQUENCE: 45
atgcttaata gtcccactat ttgtcagtat tttgtggggc gtgtgcttca acctgtcagg      60
gatcagtttc cccgatgtta catcgtttac                                      90

<210> SEQ ID NO 46
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 5C

<400> SEQUENCE: 46
atgcttaata gtcccactat ttgtcagtat tttgtggggg tgtgcttcaa cctgtcaggg      60
attcagtttc cccgatgtta catcgtttac                                      90

<210> SEQ ID NO 47
<211> LENGTH: 80
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 5E

<400> SEQUENCE: 47
atgactaaca gtcctgccat atgccagcta tatgttgacc aggcagtaga                 50
cagcagtgcc caaaagtaca aattttacac                                      80

<210> SEQ ID NO 48
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 5F

<400> SEQUENCE: 48
atgcttaata gtccaactat ttgtcagact tttgtaggtc gagctcttca accagttaga      60
gaaaagtttt cagactgtta tattattcat                                      90

<210> SEQ ID NO 49
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 5G

<400> SEQUENCE: 49
aaccagtatc aggagtttta cagccaggta gtcaggagga acttagtcat cctggtgcag      60
tggaaagggc attggattta aaggcagtct                                      90

<210> SEQ ID NO 50
<211> LENGTH: 90
<212> TYPE: DNA
<213> ORGANISM: Homo sapiens
<220> FEATURE:
```

-continued

```
<221> NAME/KEY: misc_feature
<222> LOCATION: (1)..(90)
<223> OTHER INFORMATION: Capture probe 5H

<400> SEQUENCE: 50
aacaatgtta gaatggctca cagaactcag gaaaatactt tacttgtatt taatggtttg    60
ttacataaga tacaactcaa ggaaccagct                                      90

<210> SEQ ID NO 51
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 5I

<400> SEQUENCE: 51
taccatggac gacaagcctt cgtgttacca caaggcactg caaggcaagc attgaatgtg    60
atcgtttgag ggcagggtga tcgggttaca                                      90

<210> SEQ ID NO 52
<211> LENGTH: 68
<212> TYPE: DNA
<213> ORGANISM: Homo sapiens
<220> FEATURE:
<221> NAME/KEY: misc_feature
<222> LOCATION: (1)..(68)
<223> OTHER INFORMATION: Capture probe 5J

<400> SEQUENCE: 52
tggaagggag gacttgagca cattcttaaa tgtggctcct gtaatttta acacattgac     60 acatgcta                                                              68

<210> SEQ ID NO 53
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 6A

<400> SEQUENCE: 53
atgctgaaca gtcctaccat gtgtcagtaa catgtaaatc aagctttgct ccccagtaga    60
aaataatttc ctaattgcaa gattattcat                                      90

<210> SEQ ID NO 54
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture Probe 6E

<400> SEQUENCE: 54
atgactaaca gtcctgccat atgccagcta tatgttgacc aggcagtaga gcctgttcgg    60
cagcagtgcc caaaagtaca aattttacac                                      90

<210> SEQ ID NO 55
<211> LENGTH: 90
<212> TYPE: DNA
<213> ORGANISM: Homo sapiens
```

```
<220> FEATURE:
<221> NAME/KEY: misc_feature
<222> LOCATION: (1)..(90)
<223> OTHER INFORMATION: Capture probe 6F

<400> SEQUENCE: 55
tttttaaata gtccagcatt gtttacagct gatgtagtag atttactaaa agaaatccct     60
aatgtacaag tgtatgttga tgatatatat                                     90

<210> SEQ ID NO 56
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 6G

<400> SEQUENCE: 56
gtttaaaaat agtcccaccc tgttcgaaat gcagctggcc catatcctgc agcccattcg     60
gcaagctttc ccccaatgca ctattcttca                                     90

<210> SEQ ID NO 57
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 6H

<400> SEQUENCE: 57
gtttaaaaac agccccaccc tcttcgaaca acaattagca gccgtcctca accccatgag     60
gaaaatgttt cccacatcga ccattgtcca                                     90

<210> SEQ ID NO 58
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 6I

<400> SEQUENCE: 58
atggaaagga tcaccagcaa tattccaaag tagcatgaca aaaatcttag agccttttaa     60
aaaacaaaat ccagacatag ttatctatca                                     90

<210> SEQ ID NO 59
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 6J

<400> SEQUENCE: 59
tggaaaggat caccagcaat ctttcaattc atgatgaggc aaatcttaga acctttcaga     60
aaagcaaacc cagacgtcat tctcatccaa                                     90

<210> SEQ ID NO 60
<211> LENGTH: 90
<212> TYPE: DNA
```

<213> ORGANISM: Homo sapiens
<220> FEATURE:
<221> NAME/KEY: misc_feature
<222> LOCATION: (1)..(90)
<223> OTHER INFORMATION: Capture probe 7A

<400> SEQUENCE: 60
atgcttaaca gtcttacgct atgtcagcat tttgtaggac aggcattaaa gaagcctcgg    60
aatatgtttc ctactgctta catcattcat    90

<210> SEQ ID NO 61
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 7B

<400> SEQUENCE: 61
atgctcaaca cctacgttaa gtcagcattt tgtaggaaga gcattaaagg actctcagaa    60
tatgtttccc actgcctaca tcgttcatta    90

<210> SEQ ID NO 62
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 7C

<400> SEQUENCE: 62
atgcttaaca gcattatatc agcatgttgt aggataggca ttaaaggtgc ctctgaatat    60
gtttcccaca gcctacatcc gtcattatat    90

<210> SEQ ID NO 63
<211> LENGTH: 90
<212> TYPE: DNA
<213> ORGANISM: Mus musculus
<220> FEATURE:
<221> NAME/KEY: misc_feature
<222> LOCATION: (1)..(90)
<223> OTHER INFORMATION: Capture probe 7E

<400> SEQUENCE: 63
atgaaaaata gccctacttt atgtcaaaaa tttgtggaca aagctatatt gactgtaagg    60
gataaatacc aagactcata tattgtgcat    90

<210> SEQ ID NO 64
<211> LENGTH: 90
<212> TYPE: DNA
<213> ORGANISM: Sus scrofa
<220> FEATURE:
<221> NAME/KEY: misc_feature
<222> LOCATION: (1)..(90)
<223> OTHER INFORMATION: Capture probe 7F

<400> SEQUENCE: 64
ttcaagaact ccccgaccat ctttgacgaa gccctacaca gagacctggc caacttcagg    60
atccaacacc ctcaggtgac cctcctccag    90

<210> SEQ ID NO 65
<211> LENGTH: 90

```
<212> TYPE: DNA
<213> ORGANISM: Baboon endogenous virus
<220> FEATURE:
<221> NAME/KEY: misc_feature
<222> LOCATION: (1)..(90)
<223> OTHER INFORMATION: Capture probe 7G

<400> SEQUENCE: 65
ttcaaaaact ctcccactct cttcgatgag gctctccaca gggacctcac cgacttccgg      60
acccagcatc cagaagtgac cctgctccag                                       90

<210> SEQ ID NO 66
<211> LENGTH: 90
<212> TYPE: DNA
<213> ORGANISM: Gibbon leukemia virus
<220> FEATURE:
<221> NAME/KEY: misc_feature
<222> LOCATION: (1)..(90)
<223> OTHER INFORMATION: Capture probe 7H

<400> SEQUENCE: 66
ttcaagaact ctcccactct cttcgacgag gccctccacc gagatttggc tcccttagg       60 gccctcaacc cccaggtggt gttactccaa                                       90

<210> SEQ ID NO 67
<211> LENGTH: 90
<212> TYPE: DNA
<213> ORGANISM: Moloney murine sarcoma virus
<220> FEATURE:
<221> NAME/KEY: misc_feature
<222> LOCATION: (1)..(90)
<223> OTHER INFORMATION: Capture probe 7I

<400> SEQUENCE: 67
ttcaaaaaca gtcccaccct gtttgatgag gcactgcaca gagacctagc agacttccgg      60
atccagcacc cagacttgat cctgctacag                                       90

<210> SEQ ID NO 68
<211> LENGTH: 90
<212> TYPE: DNA
<213> ORGANISM: Mason-Pfizer monkey virus
<220> FEATURE:
<221> NAME/KEY: misc_feature
<222> LOCATION: (1)..(90)
<223> OTHER INFORMATION: Capture probe 7J

<400> SEQUENCE: 68
atggccaaca gtcctacctt atgtcaaaaa tatgtggcca cagccataca taaggttaga     60
catgcctgga aacaaatgta tattatacat                                       90

<210> SEQ ID NO 69
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 8A

<400> SEQUENCE: 69
atgttaaata gtcccacagt ttgtcaaact tttgtaggca gaactatcca gcctgttaga     60
gatcagtttc cagatttgtg cagcaaaaag                                       90

<210> SEQ ID NO 70
```

-continued

```
<211> LENGTH: 90
<212> TYPE: DNA
<213> ORGANISM: Homo sapiens
<220> FEATURE:
<221> NAME/KEY: misc_feature
<222> LOCATION: (1)..(90)
<223> OTHER INFORMATION: Capture probe 8B

<400> SEQUENCE: 70
atgttaaaca gttccacagt ttgtcaaact tttgtaggca aagctatcca gctagttaga      60
gatcaatttc cagattgtta catcattcat                                      90
```